US007919670B1

(12) United States Patent
Stern et al.

(10) Patent No.: US 7,919,670 B1
(45) Date of Patent: Apr. 5, 2011

(54) TRANSGENIC MICE OVER-EXPRESSING RECEPTOR FOR ADVANCED GLYCATION ENDPRODUCT (RAGE) IN BRAIN AND USES THEREOF

(75) Inventors: David M. Stern, Great Neck, NY (US); Ann Marie Schmidt, Franklin Lakes, NJ (US); Shi Du Yan, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/638,653

(22) Filed: Aug. 14, 2000

(51) Int. Cl.
G01N 33/00 (2006.01)
A01K 67/027 (2006.01)

(52) U.S. Cl. .............................................. 800/3; 800/18

(58) Field of Classification Search ................ 800/3, 13, 800/14, 18, 22, 12
See application file for complete search history.

(56) References Cited

U.S. PATENT DOCUMENTS

| 5,387,742 A | 2/1995 | Cordell ........................... 800/12 |
| 5,864,018 A | 1/1999 | Morser et al. ............... 530/387.1 |

FOREIGN PATENT DOCUMENTS

| WO | WO 9726913 | 7/1997 |
| WO | WO 9739121 | 10/1997 |
| WO | WO 9739125 | 10/1997 |
| WO | WO 9822138 | 5/1998 |
| WO | WO 9907402 | 2/1999 |
| WO | WO 9918987 | 4/1999 |
| WO | WO 0020458 | 4/2000 |

OTHER PUBLICATIONS

Mullins et al., Transgenesis in Nonmurine Species, 1993, Hypertension, vol. 22, pp. 630-633.*
Selkoe, In the beginning . . . , Dec. 12, 1991, Nature, vol. 354, pp. 432-433.*
New and Comment, Major Setback for Alzheimer's Models, Science, vol. 255, pp. 1200-1202.*
Biotechnology, Aug. 5, 1991, vol. 11, No. 15.*
Lannfelt et al., Alzeimer's disease: molecular genetic and transgenic animal models, 1993, Behavioural Brain Research, vol. 57, pp. 207-213.*
Houdebine, LM (1994) Production of pharmaceutical proteins from transgenic animals. J. Biotechnology 34: 269-287.*
Sigmund (2000) Viewpoint: Are studies in genetically altered mice out of control? Arterioscler. Thromb. Vasc. Biol. 20: 1425-1429.*
Wall, RJ (1996) Transgenic livestock: Progress and prospects for the future. Theriogenology 45: 57-68.*

(Continued)

*Primary Examiner* — Anne-Marie Falk
(74) *Attorney, Agent, or Firm* — John P. White; Cooper & Dunham LLP

(57) ABSTRACT

The present invention provides for a transgenic non-human animal whose cells contain a DNA sequence comprising: (a) a nerve tissue specific promoter; and (b) a DNA sequence which encodes a receptor for advanced glycation endproducts (RAGE), wherein the promoter and the DNA sequence which encodes the receptor for advanced glycation endproducts (RAGE) are operatively linked to each other and integrated in the genome of the non-human animal, and wherein said non-human animal exhibits a reduced amount of cerebral tissue infarcted following a transient middle cerebral artery occlusion compared to an identical non-human animal lacking said DNA sequence.

2 Claims, 19 Drawing Sheets

OTHER PUBLICATIONS

Brett J, Schmidt A-M, Zou Y-S, Yan S-D, Weidman E, Pinsky DJ, Neeper Survey of the Distribution of a Newly Characterized Receptor for Advanced Glycation End Products in Tissues. *Am J Pathol* 1993;143:1699-1712.

Connolly ES, Winfree CJ, Stern DM, Solomon RA, Pinsky DJ: Procedural and strain-related variables significantly affect outcome in a murine model of focal cerebral ischemia. *Neurosurg* 1996;38:523-532.

Hofmann M, Drury S, Caifeng F, Qu W, Lu Y, Avila C, Kambhan N, Slattery T, McClary J, Nagashima M, Morser J, Stern D, Schmidt A-M: RAGE mediates a novel proinflammatory axis: a central cell surface receptor for S100/calgranulin polypeptides. *Cell* 1999;97:889-901.

Hori O, Brett J, Nagashima M, Nitecki D, Morser J, Stern DM, Schmidt AM: RAGE is a cellular binding site for amphoterin: mediation of neurite outgrowth and co-expression of RAGE and amphoterin in the developing nervous system. *J Biol Chem* 1995;270:25752-25761.

Hsia A, Masliah E, McConlogue L, Yu G-Q, Tatsuno G, Hu K, Kholodenkc D, Malenka R, Nicoll R, Mucke L: Plaque-independent disruption of neural circuits in Alzheimer's disease mouse models. *Proc Natl Acad Sci (USA)* 1999;96:3228-3233.

Nakashima Y, Plump A, Raines E, Breslow J, Ross R: ApoE-deficient mice develop lesions of all phases of atherosclerosis throughout the arterial tree. *Arterioscler Thromb* 1994;141:133-140.

Neeper et al, J. Biol. Chem., 267:14998-15004, 1992

Park L, Raman K, Lee K, Lu Y, Ferran L, Chow W-S, Stern D, Schmidt A-M: Suppression of accelerated diabetic atherosclerosis by soluble receptor for AGE (sRAGE). *Nature Med* 1998;4:1025-1031.

Schmidt et al, J. Biol. Chem., 267:14987-97, 1992.

Schmidt A-M, Yan S-D, Wautier J-L, Stern DM: Activation of RAGE: a mechanism for chronic dysfunction in diabetic vasculopathy and atherosclerosis. *Circ Res* 1999;84:489-497.

Stern et al. U.S. Appl. No. 09/638,649, filed Aug. 14, 2000, A Model of Alzheimer's-type Pathology Double Transgenic Mice, RAGE + Mutant APP.

White A, Zheng H, Galatis D, Maher F, Hesse L, Multhaup G, Beyreuther K, Masters C, Cappai R: Survival of cultured neurons from amyloid precursor protein knock-out mice against Alzheimer's amyloid-$\beta$, toxicity and oxidative stress. *J Neurosci* 1998;18:6207-6217.

Yan S-D, Zhu H, Zhu A, Golabek A, Roher A, Yu J, Soto C, Schmidt A-M, Stern DM, Kindy M: Receptor-dependent cell stress and amyloid accumulation in systemic amyloidosis. *Nat Med* 2000;6:643-651.

Yan S-D, Chen X, Chen M, Zhu H, Roher A, Slattery T, Zhao L, Nagashima M, Morser J, Migheli A, Nawroth P, Stern DM, Schmidt A-M: RAGE and amyloid-beta peptide neurotoxicity in Alzheimer's disease. *Nature* 1996;382:685-691.

\* cited by examiner

Figure 1
FIG. 1A
PD-huRAGE construct (5.9 kb)
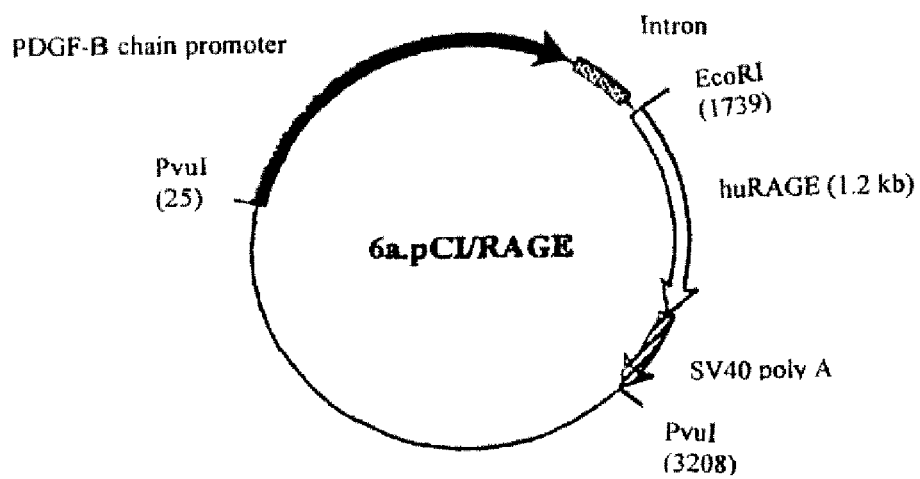
FIG. 1B
PD-huRAGE transgenic cassette (3.1 kb)
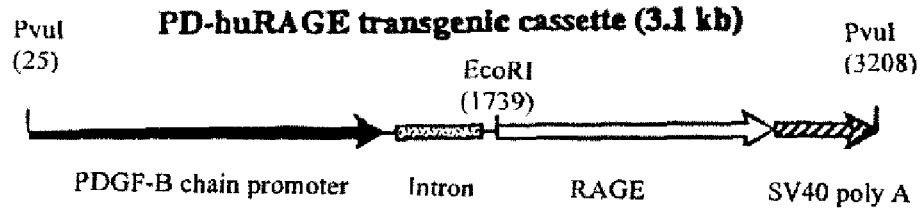

Figure 6
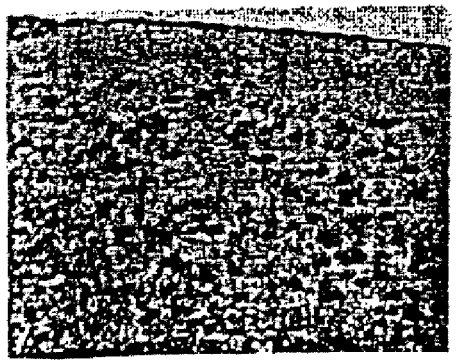 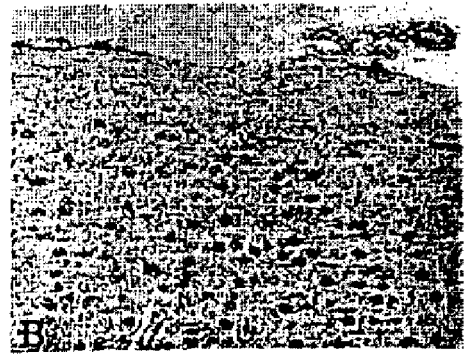
FIG. 6A        FIG. 6B

Figures 10A, 10B1, 10B2, 10B3 and 10C

Figures 14A1, 14A2, 14A3, 14A4, and 14B
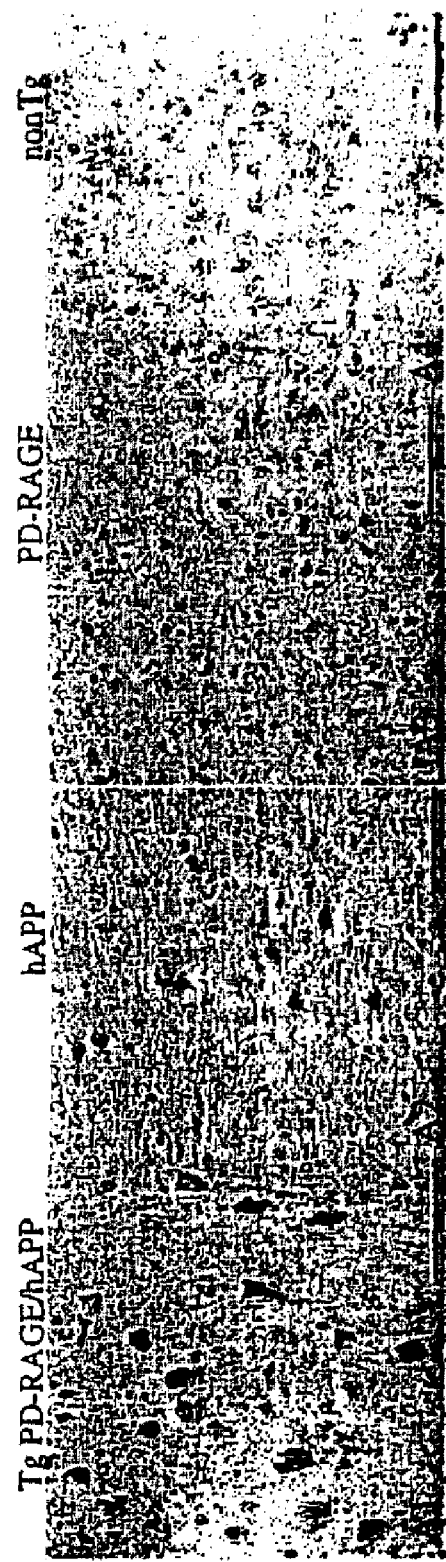
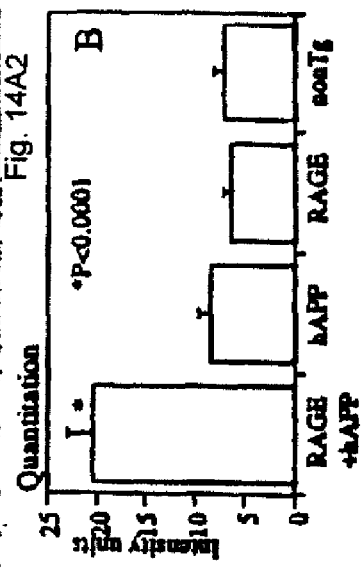

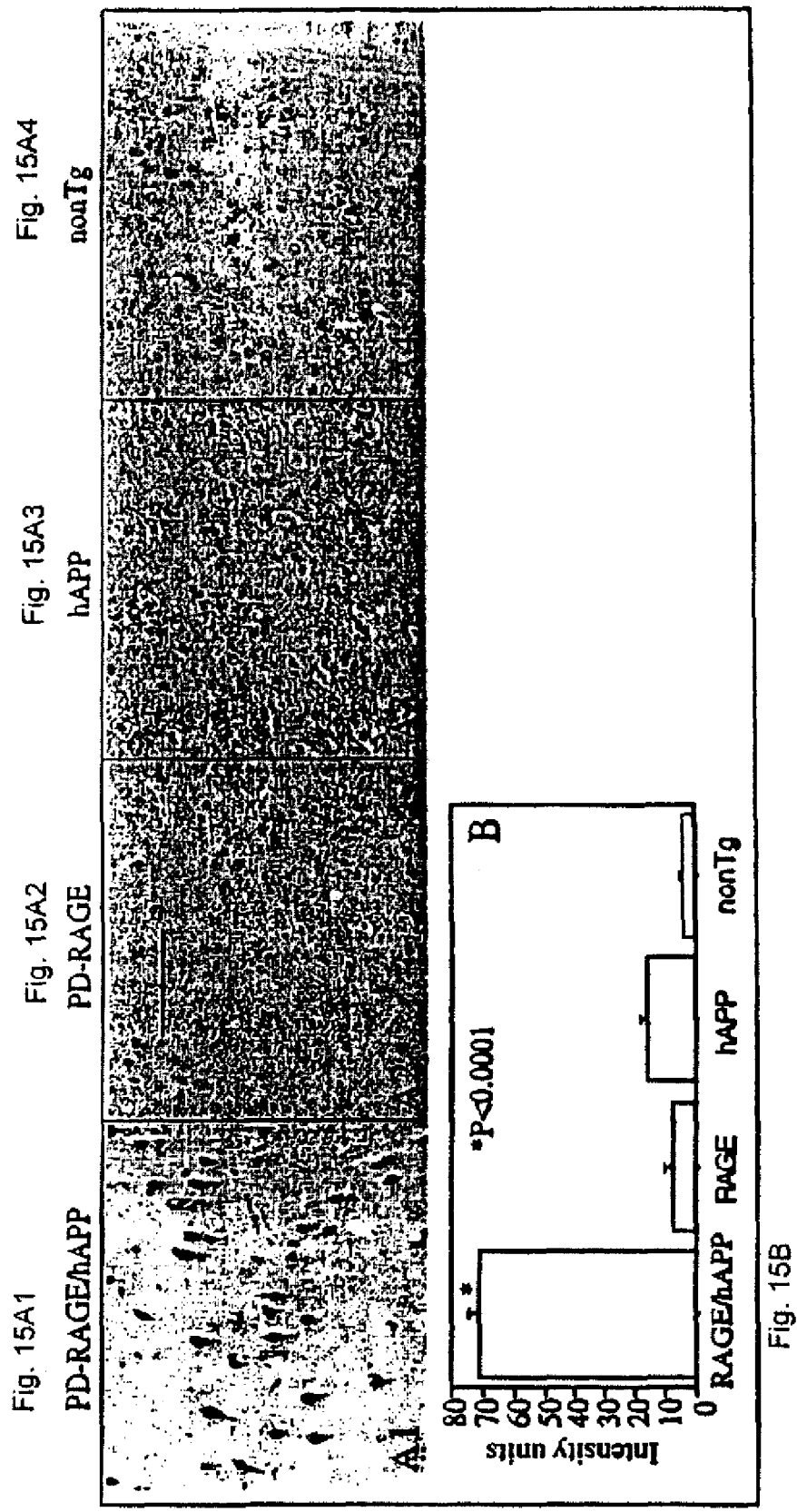
Figures 15A1, 15A2, 15A3, 15A4 and 15B

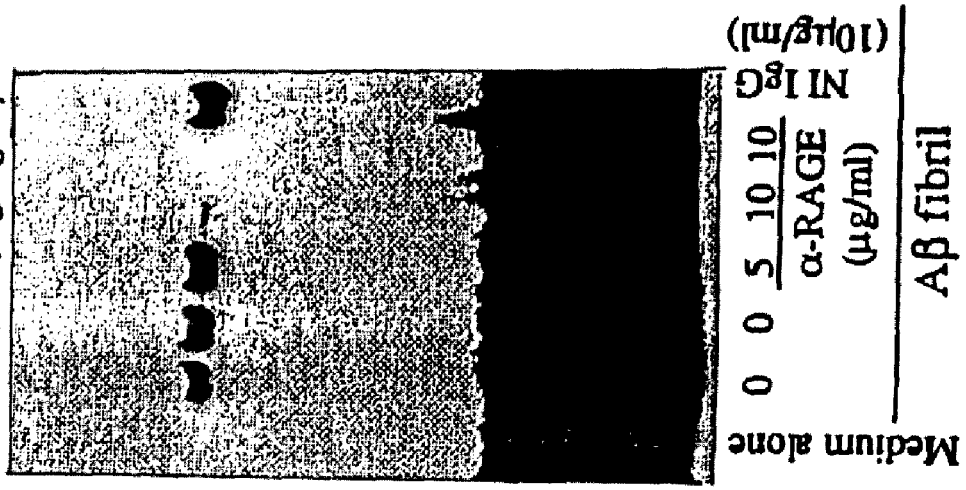
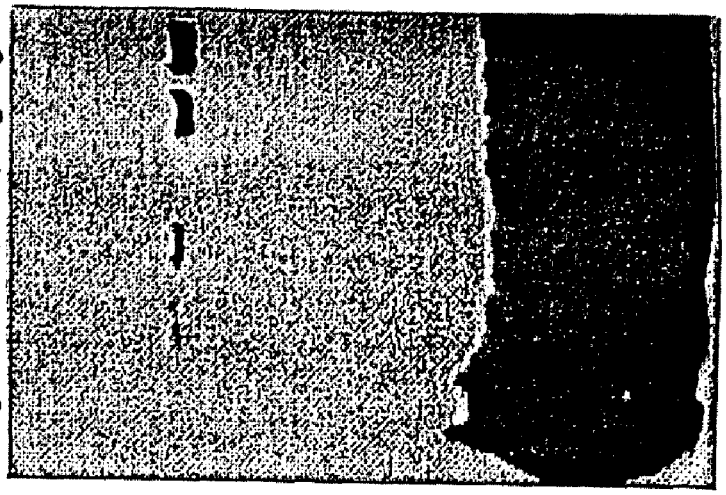
*FIGURE 17*

US 7,919,670 B1

SEQUENCE LISTING

```
<160> NUMBER OF SEQ ID NOS: 10

<210> SEQ ID NO 1
<211> LENGTH: 416
<212> TYPE: PRT
<213> ORGANISM: Bos Taurus

<400> SEQUENCE: 1

Met Ala Ala Gly Ala Val Val Gly Ala Trp Met Leu Val Leu Ser Leu
  1               5                  10                  15

Gly Gly Thr Val Thr Gly Asp Gln Asn Ile Thr Ala Arg Ile Gly Lys
                 20                  25                  30

Pro Leu Val Leu Asn Cys Lys Gly Ala Pro Lys Lys Pro Pro Gln Gln
             35                  40                  45

Leu Glu Trp Lys Leu Asn Thr Gly Arg Thr Glu Ala Trp Lys Val Leu
         50                  55                  60

Ser Pro Gln Gly Asp Pro Trp Asp Ser Val Ala Arg Val Leu Pro Asn
 65                  70                  75                  80

Gly Ser Leu Leu Leu Pro Ala Val Gly Ile Gln Asp Glu Gly Thr Phe
                 85                  90                  95
```

```
Arg Cys Arg Ala Thr Ser Arg Ser Gly Lys Glu Thr Lys Ser Asn Tyr
        100                 105                 110

Arg Val Arg Val Tyr Gln Ile Pro Gly Lys Pro Glu Ile Val Asp Pro
        115                 120                 125

Ala Ser Glu Leu Met Ala Gly Val Pro Asn Lys Val Gly Thr Cys Val
130                 135                 140

Ser Glu Gly Gly Tyr Pro Ala Gly Thr Leu Asn Trp Leu Leu Asp Gly
145                 150                 155                 160

Lys Thr Leu Ile Pro Asp Gly Lys Gly Val Ser Val Lys Glu Thr
                165                 170                 175

Lys Arg His Pro Lys Thr Gly Leu Phe Thr Leu His Ser Glu Leu Met
        180                 185                 190

Val Thr Pro Ala Arg Gly Gly Ala Leu His Pro Thr Phe Ser Cys Ser
        195                 200                 205

Phe Thr Pro Gly Leu Pro Arg Arg Arg Ala Leu His Thr Ala Pro Ile
210                 215                 220

Gln Leu Arg Val Trp Ser Glu His Arg Gly Gly Glu Gly Pro Asn Val
225                 230                 235                 240

Asp Ala Val Pro Leu Lys Glu Val Gln Leu Val Glu Pro Glu Gly
                245                 250                 255

Gly Ala Val Ala Pro Gly Gly Thr Val Thr Leu Thr Cys Glu Ala Pro
        260                 265                 270

Ala Gln Pro Pro Pro Gln Ile His Trp Ile Lys Asp Gly Arg Pro Leu
        275                 280                 285

Pro Leu Pro Pro Gly Pro Met Leu Leu Leu Pro Glu Val Gly Pro Glu
        290                 295                 300

Asp Gln Gly Thr Tyr Ser Cys Val Ala Thr His Pro Ser His Gly Pro
305                 310                 315                 320

Gln Glu Ser Arg Ala Val Ser Val Thr Ile Ile Glu Thr Gly Glu Glu
                325                 330                 335

Gly Thr Thr Ala Gly Ser Val Glu Gly Pro Gly Leu Glu Thr Leu Ala
        340                 345                 350

Leu Thr Leu Gly Ile Leu Gly Gly Leu Gly Thr Val Ala Leu Leu Ile
        355                 360                 365

Gly Val Ile Val Trp His Arg Arg Gln Arg Lys Gly Gln Glu Arg
        370                 375                 380

Lys Val Pro Glu Asn Gln Glu Glu Glu Glu Glu Arg Ala Glu Leu
385                 390                 395                 400

Asn Gln Pro Glu Glu Pro Glu Ala Ala Glu Ser Ser Thr Gly Pro
                405                 410                 415
```

<210> SEQ ID NO 2
<211> LENGTH: 1426
<212> TYPE: DNA
<213> ORGANISM: Bos Taurus

<400> SEQUENCE: 2

```
cggagaagga tggcagcagg ggcagtggtc ggagcctgga tgctagtcct cagtctgggg    60
gggacagtca cggggggacca aaacatcaca gcccggatcg ggaagccact ggtgctgaac   120
tgcaaggagg cccccaagaa accaccccag cagctggaat ggaaactgaa cacaggccgg   180
acagaagctt ggaaagtcct gtctccccag ggagaccctg ggatagcgt ggctcgggtc    240 ctccccaacg gctccctcct cctgccggct gttgggatcc aggatgaggg gactttccgg   300
tgccgggcaa cgagccggag cggaaaggag accaagtcta actaccgagt ccgagtctat   360
```

```
cagattcctg ggaagccaga aattgttgat cctgcctctg aactcatggc tggtgtcccc    420
aataaggtgg ggacatgtgt gtccgagggg ggctaccctg cagggactct taactggctc    480
ttggatggga aaactctgat tcctgatggc aaaggagtgt cagtgaagga agagaccaag    540
agacacccaa agacagggct tttcacgctc cattcggagc tgatggtgac cccagctcgg    600
ggaggagctc tccaccccac cttctcctgt agcttcaccc ctggccttcc ccggcgccga    660
gccctgcaca cggcccccat ccagctcagg gtctggagtg agcaccgagg tggggagggc    720
cccaacgtgg acgctgtgcc actgaaggaa gtccagttgg tggtagagcc agaaggggga    780
gcagtagctc ctggtggtac tgtgaccttg acctgtgaag cccccgccca gcccccacct    840
caaatccact ggatcaagga tggcaggccc ctgcccttc ccctggccc catgctgctc    900 ctcccagagg tagggcctga ggaccaggga acctacagtt gtgtggccac ccatcccagc    960
catgggcccc aggagagccg tgctgtcagc gtcacgatca tcgaaacagg cgaggagggg   1020
acgactgcag gctctgtgga agggccgggg ctggaaaccc tagccctgac cctggggatc   1080 ctggaggcc tggggacagt cgccctgctc attggggtca tcgtgtggca tcgaaggcgg   1140
caacgcaaag acaggagag gaaggtcccg gaaaaccagg aggaggaaga ggaggagaga   1200
gcggaactga accagccaga ggagcccgag gcggcagaga gcagcacagg agggccttga   1260
ggagcccacg gccagacccg atccatcagc cccttttctt ttcccacact ctgttctggc   1320
cccagaccag ttctcctctg tataatctcc agcccacatc tcccaaactt tcttccacaa   1380
ccagagcctc ccacaaaaag tgatgagtaa acacctgcca cattta               1426

<210> SEQ ID NO 3
<211> LENGTH: 404
<212> TYPE: PRT
<213> ORGANISM: Human

<400> SEQUENCE: 3

Gly Ala Ala Gly Thr Ala Val Gly Ala Trp Val Leu Val Leu Ser Leu
 1               5                  10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Arg Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190
```

```
Met Val Thr Pro Ala Arg Gly Gly Asp Pro Arg Pro Thr Phe Ser Cys
            195                 200                 205
Ser Phe Ser Pro Gly Leu Pro Arg His Arg Ala Leu Arg Thr Ala Pro
            210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
            260                 265                 270
Lys Asp Gly Val Pro Leu Pro Leu Pro Pro Ser Pro Val Leu Ile Leu
            275                 280                 285
Pro Glu Ile Gly Pro Gln Asp Gln Gly Thr Tyr Ser Cys Val Ala Thr
            290                 295                 300
His Ser Ser His Gly Pro Gln Glu Ser Arg Ala Val Ser Ile Ser Ile
305                 310                 315                 320
Ile Glu Pro Gly Glu Gly Pro Thr Ala Gly Ser Val Gly Gly Ser
                325                 330                 335
Gly Leu Gly Thr Leu Ala Leu Ala Leu Gly Ile Leu Gly Gly Leu Gly
            340                 345                 350
Thr Ala Ala Leu Leu Ile Gly Val Ile Leu Trp Gln Arg Arg Gln Arg
            355                 360                 365
Arg Gly Glu Glu Arg Lys Ala Pro Glu Asn Gln Glu Glu Glu Glu Glu
            370                 375                 380
Arg Ala Glu Leu Asn Gln Ser Glu Glu Pro Glu Ala Gly Glu Ser Ser
385                 390                 395                 400
Thr Gly Gly Pro

<210> SEQ ID NO 4
<211> LENGTH: 1391
<212> TYPE: DNA
<213> ORGANISM: Human

<400> SEQUENCE: 4
ggggcagccg gaacagcagt tggagcctgg gtgctggtcc tcagtctgtg gggggcagta       60
gtaggtgctc aaaacatcac agcccggatt ggcgagccac tggtgctgaa gtgtaagggg     120
gcccccaaga aaccacccca gcggctggaa tggaaactga acacaggccg acagaagct      180
tggaaggtcc tgtctcccca gggaggaggc cctgggaca gtgtggctcg tgtccttccc      240
aacggctccc tcttccttcc ggctgtcggg atccaggatg aggggatttt ccggtgcagg     300
gcaatgaaca ggaatggaaa ggagaccaag tccaactacc gagtccgtgt ctaccagatt     360
cctgggaagc cagaaattgt agattctgcc tctgaactca cggctggtgt tcccaataag     420
gtggggacat gtgtgtcaga gggaagctac cctgcaggga ctcttagctg gcacttggat     480
gggaagcccc tggtgcctaa tgagaaggga gtatctgtga aggaacagac caggagacac     540
cctgagacag gctcttcac actgcagtcg gagctaatgg tgaccccagc ccggggagga     600
gatccccgtc ccaccttctc ctgtagcttc agcccaggcc ttccccgaca ccgggccttg     660
cgcacagccc ccatccagcc ccgtgtctgg gagcctgtgc ctctggagga ggtccaattg     720
gtggtggagc cagaaggtgg agcagtagct cctggtggaa ccgtaaccct gacctgtgaa     780
gtccctgccc agcctctcc tcaaatccac tggatgaagg atggtgtgcc cttgcccctt     840
cccccccagcc ctgtgctgat cctccctgag atagggcctc aggaccaggg aacctacagc     900
```

-continued

```
tgtgtggcca cccattccag ccacgggccc caggaaagcc gtgctgtcag catcagcatc    960
atcgaaccag gcgaggaggg gccaactgca ggctctgtgg gaggatcagg gctgggaact   1020
ctagccctgg ccctggggat cctgggaggc ctggggacag ccgccctgct cattggggtc   1080
atcttgtggc aaaggcggca acgccgagga gaggagagga aggcccccaga aaaccaggag   1140 gaagaggagg agcgtgcaga actgaatcag tcggaggaac ctgaggcagg cgagagtagt   1200
actggagggc cttgagggc ccacagacag atcccatcca tcagctccct tttcttttc    1260 ccttgaactg ttctggcctc agaccaactc tctcctgtat aatctctctc ctgtataacc   1320
ccaccttgcc aagctttctt ctacaaccag agcccccac aatgatgatt aaacacctga    1380
cacatcttgc a                                                         1391
```

<210> SEQ ID NO 5
<211> LENGTH: 403
<212> TYPE: PRT
<213> ORGANISM: Murine

<400> SEQUENCE: 5

Met Pro Ala Gly Thr Ala Ala Arg Ala Trp Val Leu Val Leu Ala Leu
1               5                   10                  15

Trp Gly Ala Val Ala Gly Gly Gln Asn Ile Thr Ala Arg Ile Gly Glu
                20                  25                  30

Pro Leu Val Leu Ser Cys Lys Gly Ala Pro Lys Lys Pro Gln Gln
            35                  40                  45

Leu Glu Trp Lys Leu Asn Thr Gly Arg Thr Glu Ala Trp Lys Val Leu
        50                  55                  60

Ser Pro Gln Gly Gly Pro Trp Asp Ser Val Ala Gln Ile Leu Pro Asn
65                  70                  75                  80

Gly Ser Leu Leu Leu Pro Ala Thr Gly Ile Val Asp Glu Gly Thr Phe
                85                  90                  95

Arg Cys Arg Ala Thr Asn Arg Arg Gly Lys Glu Val Lys Ser Asn Tyr
            100                 105                 110

Arg Val Arg Val Tyr Gln Ile Pro Gly Lys Pro Glu Ile Val Asp Pro
        115                 120                 125

Ala Ser Glu Leu Thr Ala Ser Val Pro Asn Lys Val Gly Thr Cys Val
    130                 135                 140

Ser Glu Gly Ser Tyr Pro Ala Gly Thr Leu Ser Trp His Leu Asp Gly
145                 150                 155                 160

Lys Leu Leu Ile Pro Asp Gly Lys Glu Thr Leu Val Lys Glu Glu Thr
                165                 170                 175

Arg Arg His Pro Glu Thr Gly Leu Phe Thr Leu Arg Ser Glu Leu Thr
            180                 185                 190

Val Ile Pro Thr Gln Gly Gly Thr Thr His Pro Thr Phe Ser Cys Ser
        195                 200                 205

Phe Ser Leu Gly Leu Pro Arg Arg Arg Pro Leu Asn Thr Ala Pro Ile
    210                 215                 220

Gln Leu Arg Val Arg Glu Pro Gly Pro Pro Glu Gly Ile Gln Leu Leu
225                 230                 235                 240

Val Glu Pro Glu Gly Gly Ile Val Ala Pro Gly Gly Thr Val Thr Leu
                245                 250                 255

Thr Cys Ala Ile Ser Ala Gln Pro Pro Pro Gln Val His Trp Ile Lys
            260                 265                 270

Asp Gly Ala Pro Leu Pro Leu Ala Pro Ser Pro Val Leu Leu Leu Pro
        275                 280                 285

```
Glu Val Gly His Ala Asp Glu Gly Thr Tyr Ser Cys Val Ala Thr His
    290                 295                 300

Pro Ser His Gly Pro Gln Glu Ser Pro Pro Val Ser Ile Arg Val Thr
305                 310                 315                 320

Glu Thr Gly Asp Glu Gly Pro Ala Glu Gly Ser Val Gly Glu Ser Gly
                325                 330                 335

Leu Gly Thr Leu Ala Leu Ala Leu Gly Ile Leu Gly Gly Leu Gly Val
            340                 345                 350

Val Ala Leu Leu Val Gly Ala Ile Leu Trp Arg Lys Arg Gln Pro Arg
            355                 360                 365

Arg Glu Glu Arg Lys Ala Pro Glu Ser Gln Glu Asp Glu Glu Glu Arg
        370                 375                 380

Ala Glu Leu Asn Gln Ser Glu Glu Ala Glu Met Pro Glu Asn Gly Ala
385                 390                 395                 400

Gly Gly Pro

<210> SEQ ID NO 6
<211> LENGTH: 1348
<212> TYPE: DNA
<213> ORGANISM: Murine

<400> SEQUENCE: 6
gcaccatgcc agcggggaca gcagctagag cctgggtgct ggttcttgct ctatggggag      60
ctgtagctgg tggtcagaac atcacagccc ggattggaga gccacttgtg ctaagctgta    120
agggggcccc taagaagccg ccccagcagc tagaatggaa actgaacaca ggaagaactg    180
aagcttggaa ggtcctctct ccccagggag gcccctggga cagcgtggct caaatcctcc    240
ccaatggttc cctcctcctt ccagccactg gaattgtcga tgaggggacg ttccggtgtc    300
gggcaactaa caggcgaggg aaggaggtca gtccaactac cgagtccga gtctaccaga     360 ttcctgggaa gccagaaatt gtggatcctg cctctgaact cacagccagt gtccctaata    420
aggtggggac atgtgtgtct gagggaagct accctgcagg gacccttagc tggcacttag    480
atgggaaact tctgattccc gatggcaaag aaacactcgt gaaggaagag accaggagac    540
accctgagac gggactcttt acactgcggt cagagctgac agtgatcccc acccaaggag    600
gaaccaccca tcctaccttc tcctgcagtt tcagcctggg ccttcccgg cgcagacccc     660 tgaacacagc ccctatccaa ctccgagtca gggagcctgg gcctccagag ggcattcagc    720
tgttggttga gcctgaaggt ggaatagtcg ctcctggtgg gactgtgacc ttgacctgtg    780
ccatctctgc ccagccccct cctcaggtcc actggataaa ggatggtgca cccttgcccc    840
tggctcccag ccctgtgctg ctcctccctg aggtggggca gcggatgag ggcacctata      900 gctgcgtggc cacccaccct agccacggac ctcaggaaag ccctcctgtc agcatcaggg    960
tcacagaaac cggcgatgag gggccagctg aaggctctgt gggtgagtct gggctggta   1020 cgctagccct ggccttgggg atcctgggag gcctgggagt agtagccctg ctcgtcgggg    1080
ctatcctgtg gcgaaaacga caacccaggc gtgaggagag aaggccccg gaaagccagg    1140 aggatgagga ggaacgtgca gagctgaatc agtcagagga agcggagatg ccagagaatg    1200
gtgccggggg accgtaagag cacccagatc gagcctgtgt gatggcccta gagcagctcc    1260
cccacattcc atcccaattc ctccttgagg cacttccttc tccaaccaga gcccacatga    1320
tccatgctga gtaaacattt gatacggc                                      1348

<210> SEQ ID NO 7
<211> LENGTH: 24
```

-continued

```
<212> TYPE: DNA
<213> ORGANISM: Artificial Sequence
<220> FEATURE:
<223> OTHER INFORMATION: Description of Artificial Sequence:    Synthetic
      PCR Primers

<400> SEQUENCE: 7
agcggctgga atggaaactg aaca                                              24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:    Synthetic
      PCR Primers

<400> SEQUENCE: 8 gaagggcaa gggcacacca tc                                                 22

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:    Synthetic
      PCR Primers

<400> SEQUENCE: 9
gacaagtatc tcgagacacc tggggatgag                                        30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:    Synthetic
      PCR Primers

<400> SEQUENCE: 10
aaagaacttg taggttggat tttcgtacc                                         29
```

TRANSGENIC MICE OVER-EXPRESSING RECEPTOR FOR ADVANCED GLYCATION ENDPRODUCT (RAGE) IN BRAIN AND USES THEREOF

BACKGROUND OF THE INVENTION

Throughout this application, various publications are referenced by number. Full citations for these publications may be found listed at the end of the specification immediately preceding the claims. The disclosures of these publications in their entireties are hereby incorporated by reference into this application in order to more fully describe the state of the art as known to those skilled therein as of the date of the invention described and claimed herein.

The pain of Alzheimer's disease results directly from the memory loss and cognitive deficits suffered by the patient. These eventually result in the patient's loss of identity, autonomy, and freedom. As a step toward curing this disease, alleviating its symptoms, or retarding its progression, it would be desirable to develop a transgenic animal model exhibiting the main debilitating phenotype of Alzheimer's disease, that is, memory loss, expressed concomitantly with the neuropathological correlates of Alzheimer's disease, for example, beta-amyloid accumulation, increased glial reactivity, and hippocampal cell loss.

It is estimated that over 5% of the U.S. population over 65 and over 15% of the U.S. population over 85 are beset with some form of Alzheimer's disease (Cross, A. J., Eur J Pharmacol (1982) 82:77-80; Terry, R. D., et al., Ann Neurol (1983) 14:497506). It is believed that the principal cause for confinement of the elderly in long term care facilities is due to this disease, and approximately 65% of those dying in skilled nursing facilities suffer from it.

Certain facts about the biochemical and metabolic phenomena associated with the presence of Alzheimer's disease are known. Two morphological and histopathological changes noted in Alzheimer's disease brains are neurofibrillary tangles (NFT) and amyloid deposits. Intraneuronal neurofibrillary tangles are present in other degenerative diseases as well, but the presence of amyloid deposits both in the interneuronal spaces (neuritic plaques) and in the surrounding microvasculature (vascular plaques) seems to be characteristic of Alzheimer's. Of these, the neuritic plaques seem to be the most prevalent (Price, D. L., et al., Drug Development Research (1985) 5:59-68). Plaques are also seen in the brains of aged Down's Syndrome patients who develop Alzheimer's disease.

SUMMARY OF THE INVENTION

The present invention provides for a transgenic non-human animal whose cells contain a DNA sequence comprising: (a) a nerve tissue specific promoter; and (b) a DNA sequence which encodes a receptor for advanced glycation endproducts (RAGE), wherein the promoter and the DNA sequence which encodes the receptor for advanced glycation endproducts (RAGE) are operatively linked to each other and integrated in the genome of the non-human animal, and wherein said non-human animal exhibits a reduced amount of cerebral tissue infarcted following a transient middle cerebral artery occlusion compared to an identical non-human animal lacking said DNA sequence.

BRIEF DESCRIPTION OF THE FIGURES

FIGS. 1A-1B. Schematic depiction of strategy for making Tg PD-RAGE mice.

FIGS. 4A-4B. RAGE expression in Tg PD-RAGE mice (+) compared with nontransgenic littermate controls (-). A (Northern) and B (Western) analysis of homogenates of cerebral cortex. Equal amounts of RNA (note approximately equal intensity of 28S ribosomal RNA band on the ethidium bromide stained gel) and protein were loaded in each lane.

FIGS. 6A-6B. Immunohistochemical identification of RAGE in cerebral cortex from a Tg PD-RAGE mouse (FIG. 6A) and a nontransgenic littermate control (FIG. 6B).

FIGS. 9A, 9B1, 9B2, 9B3, 9C. Increased expression of M-CSF in cerebral cortex from double Tg mice overexpressing RAGE and mutant human APP (hAPP). FIG. 9A, Northern analysis for M-CSF transcripts. FIGS. 9B1-9B3, immunostaining for M-CSF. FIG. 9C, Quantitation of immunocytochemical results.

FIGS. 10A, 10B1, 10B2, 10B3, 10C. Increased expression of Interleukin (IL)-6 in cerebral cortex from double Tg mice overexpressing RAGE and mutant human APP (hAPP). FIG. 10A, Northern analysis for IL-6 transcripts. FIGS. 10B1-10B3, immunostaining for IL-6. FIG. 10C, Quantitation of immunocytochemical results.

FIGS. 14A1, 14A2, 14A3, 14A4, and 14B. Increased expression of activated caspase-3 in cerebral cortex from Tg PD-RAGE/hAPP mice. FIGS. 14A1-4, immunostaining for activated caspase-3. FIG. 14B, quantitation of immunocytochemical results from multiple fields of all mice in each of the experimental groups. Scale bar, 10 μm.

FIGS. 15A1, 15A2, 15A3, 15A4, and 15B. Immunostaining (FIGS. 15A1-4) with antibody to phosphorylated tau (AT8) in cerebral cortex of the indicated transgenic mice. FIG. 15B demonstrates image analysis of multiple microscopic fields from all of the mice in each of the experimental groups. Scale bar, 10 μm.

FIGS. 17A-17B. NF-kB activation in primary cortical neuron cultures from Tg PD-RAGE and nontransgenic littermates exposed for 5 hrs to preformed Aβ(1-40) fibrils (500 nM) alone (FIG. 17A (left panel)) or in the presence of anti-RAGE IgG or nonimmune (NI) IgG (FIG. 17B (right panel)). Gel shift analysis was performed with $^{32}$P-labelled NF-kB probe.

DETAILED DESCRIPTION OF THE INVENTION

Figure 2:
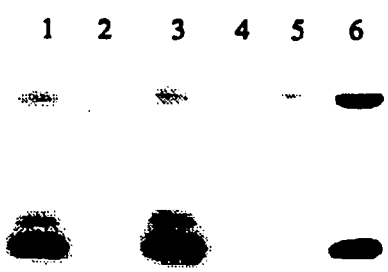
FIG. 2. Southern analysis of three founders for Tg PD-RAGE mice: lanes 1, 3, 6 show mice positive for the transgene and lanes 2, 4-5 are nontransgenic littermates.

The present invention provides for a transgenic non-human animal whose cells contain a DNA sequence comprising: (a) a nerve tissue specific promoter; and (b) a DNA sequence which encodes a receptor for advanced glycation endproducts (RAGE), wherein the promoter and the DNA sequence which encodes the receptor for advanced glycation endproducts (RAGE) are operatively linked to each other and integrated in the genome of the non-human animal, and wherein said non-human animal exhibits a reduced amount of cerebral tissue infarcted following a transient middle cerebral artery occlusion compared to an identical non-human animal lacking said DNA sequence.

In one embodiment of the invention, the promoter is platelet derived growth factor (PDGF)-B-chain promoter. In another embodiment of the invention, the DNA sequence which encodes amyloid-beta peptide alcohol dehydrogenase is a human DNA sequence. In another embodiment, the reduction of infarcted cerebral tissue is about a 50% reduction. In another embodiment, the transgenic non-human animal is a mouse, a rat, a sheep, a dog, a primate, or a reptile. In another embodiment of the invention, the non-human animal is a mammal.

This invention also provides for a method for evaluating in a non-human transgenic animal the potential therapeutic effect of an agent for treating Alzheimer's disease in a human, which comprises: (a) administering an agent to a transgenic non-human animal whose cells comprise a nerve tissue specific promoter operatively linked to a DNA sequence which encodes receptor for advanced glycation endproducts (RAGE); and (b) determining the therapeutic effect of the agent on the transgenic non-human animal by monitoring basal synaptic transmission or synaptic plasticity, wherein an increase in basal synaptic transmission or synaptic plasticity indicates that the agent would have a potential therapeutic effect on Alzheimer's disease in a human.

The invention also provides for a method for identifying whether an agent or a compound is an inhibitor of receptor for advanced glycation endproduct (RAGE) in vivo, which comprises (a) obtaining a non-human transgenic animal whose cells overexpress RAGE in neurons; (b) administering an agent or compound to the transgenic non-human animal; (c) determining whether the transgenic non-human animal from step (b) exhibits a change in neuronal function from an identical transgenic non-human animal which was not administered the agent or compound; wherein a determination of change in neuronal function indicates that the agent or compound is an inhibitor of RAGE in vivo.

In one embodiment of the invention, the promoter of both element (a) and (b) is platelet derived growth factor (PDGF)-B-chain promoter.

In another embodiment of the invention, the non-human animal is a mouse, a rat, a sheep, a dog, a primate, or a reptile. In another embodiment, the animal is a mammal.

The phenotype observed in the transgenic RAGE overexpressing mice described herein was not obvious prior to the creation of such mice. The transgenic mice described herein only overexpress RAGE in neurons, whereas in the normal animal, RAGE is also expressed in the microglia at high levels (the microglia are considered important cells in the pathogenesis of Alzheimer's disease). Therefore, prior to creating and studying the actual transgenic, one could have imagined that overexpression of RAGE in neurons alone would not have had a significant effect on the resulting transgenic animal. However, as described hereinbelow, there is evidence that RAGE overexpressing mice exhibit a reduced neurologic deficit score and that RAGE overexpressing mice have a reduced volume of infarcted cerebral tissue when subjected to the transient middle cerebral artery occlusion procedure (described below).

Nucleotide and Amino Acid sequences of RAGE

The nucleotide and protein (amino acid) sequences for RAGE (both human and murine and bovine) are known. The following references which recite these sequences are incorporated by reference:

Schmidt et al, Biol. Chem., 267:14987-97, 1992
Neeper et al, J. Biol. Chem., 267:14998-15004, 1992

RAGE sequences (DNA sequence and translation) from bovine, murine and *homo sapien* are listed hereinbelow. These sequences are available from GenBank as are other sequences of RAGE from other species:

LOCUS BOVRAGE 1426 by mRNA MAM 09-DEC-1993
DEFINITION Cow receptor for advanced glycosylation end products (RAGE) mRNA, complete cds.
ACCESSION M91212 VERSION M91212.1 GI:163650
KEYWORDS RAGE; cell surface receptor.
SOURCE Bos taurus cDNA to mRNA. ORGANISM *Bos taurus* Eukaryota; Metazoa; Chordata; Craniata; Vertebrata; Euteleostomi; Mammalia; Eutheria; Cetartiodactyla; Ruminantia; Pecora; Bovoidea; Bovidae; Bovinae; Bos.
REFERENCE 1 (bases 1 to 1426) AUTHORS Neeper, M., Schmidt, A. M., Brett, J., Yan, S. D., Wang, F., Pan, Y. C., Elliston, K., Stern, D. and Shaw, A. TITLE Cloning and expression of a cell surface receptor for advanced glycosylation end products of proteins
JOURNAL J. Biol. Chem. 267, 14998-15004 (1992)
MEDLINE 92340547 REFERENCE 2 (bases 1 to 1426) AUTHORS Shaw, A. TITLE Direct Submission JOURNAL Submitted (15-APR-1992) A. Shaw, Department of Cellular and Molecular Biology, Merck Sharp and Dohme Research Laboratories, West Point, Pa. 19486
USA FEATURES Location/Qualifiers source 1..1426 /organism="*Bos taurus*" /db_xref="taxon:9913" /tissue_type="lung" CDS 10..1260 /standard_name="RAGE" /codon_start=1 /product="receptor for advanced glycosylation end products" /protein_id="AAA03575.1" /db_xref="GI:163651" /translation="

(SEQ ID NO: 1)
MAAGAVVGAWMLVLSLGGTVTGDQNITARIGKPLVLNCKGAPKKPPQQLE

WKLNTGRTEAWKVLSPQGDPWDSVARVLPNGSLLLPAVGIQDEGTFRCRA

-continued

```
TSRSGKETKSNYRVRVYQIPGKPEIVDPASELMAGVPNKVGTCVSEGGYP

AGTLNWLLDGKTLIPDGKGVSVKEETKRHPKTGLFTLHSELMVTPARGGA

LHPTFSCSFTPGLPRRRALHTAPIQLRVWSEHRGGEGPNVDAVPLKEVQL

VVEPEGGAVAPGGTVTLTCEAPAQPPPQIHWIKDGRPLPLPPGPMLLLPE

VGPEDQGTYSCVATHPSHGPQESRAVSVTIIETGEEGTTAGSVEGPGLET

LALTLGILGGLGTVALLIGVIVWHRRRQRKGQERKVPENQEEEEERAEL

NQPEEPEAAESSTGGP
``` polyA_signal 1406..1411 polyA_site 1426
BASE COUNT 322 a 429 c 440 g 235 t

```
ORIGIN
   1 cggagaagga tggcagcagg ggcagtggtc ggagcctgga tgctagtcct cagtctgggg   (SEQ ID NO: 2)

61 gggacagtca cggggggacca aaacatcaca gcccggatcg ggaagccact ggtgctgaac 121 tgcaagggag cccccaagaa accaccccag cagctggaat ggaaactgaa cacaggccgg 181 acagaagctt ggaaagtcct gtctccccag ggagacccct gggatagcgt ggctcgggtc 241 ctccccaacg gctccctcct cctgccggct gttgggatcc aggatgaggg gactttccgg 301 tgccgggcaa cgagccggag cggaaggag accaagtcta actaccgagt ccgagtctat 361 cagattcctg ggaagccaga aattgttgat cctgcctctg aactcatggc tggtgtcccc 421 aataaggtgg ggacatgtgt gtccgagggg ggctaccctg cagggactct taactggctc 481 ttggatggga aaactctgat tcctgatggc aaaggagtgt cagtgaagga agagaccaag 541 agacacccaa agacagggct tttcacgctc cattcggagc tgatggtgac cccagctcgg 601 ggaggagctc tccaccccac cttctcctgt agcttcaccc ctggccttcc ccggcgccga 661 gccctgcaca cggcccccat ccagctcagg gtctggagtg agcaccgagg tggggagggc 721 cccaacgtgg acgctgtgcc actgaaggaa gtccagttgg tggtagagcc agaaggggga 781 gcagtagctc ctggtggtac tgtgaccttg acctgtgaag cccccgccca gcccccacct 841 caaatccact ggatcaagga tggcaggccc ctgccccttc cccctggccc catgctgctc 901 ctcccagagg tagggcctga ggaccaggga acctacagtt gtgtggccac ccatcccagc 961 catgggcccc aggagagccg tgctgtcagc gtcacgatca tcgaaacagg cgaggagggg 1021 acgactgcag gctctgtgga agggccgggg ctggaaaccc tagccctgac cctggggatc 1081 ctgggaggcc tggggacagt cgccctgctc attggggtca tcgtgtggca tcgaaggcgg 1141 caacgcaaag gacaggagag gaaggtcccg gaaaaccagg aggaggaaga ggaggagaga 1201 gcggaactga accagccaga ggagcccgag gcggcagaga gcagcacagg agggccttga 1261 ggagcccacg gccagacccg atccatcagc cccttttctt ttcccacact ctgttctggc 1321 cccagaccag ttctcctctg tataatctcc agcccacatc tcccaaactt tcttccacaa 1381 ccagagcctc ccacaaaaag tgatgagtaa acacctgcca cattta//
```

LOCUS HUMRAGE 1391 by mRNA PRI 9 Dec. 1993
DEFINITION Human receptor for advanced glycosylation end products (RAGE) mRNA, partial cds.
ACCESSION M91211 VERSION M91211.1 GI:190845
KEYWORDS RAGE; cell surface receptor.
SOURCE Homo sapiens cDNA to mRNA.
ORGANISM Homo sapiens Eukaryota; Metazoa; Chordata; Craniata; Vertebrata; Euteleostomi; Mammalia; Eutheria; Primates; Catarrhini; Hominidae; Homo.

REFERENCE 1 (bases 1 to 1391)
AUTHORS Neeper, M., Schmidt, A. M., Brett, J., Yan, S. D., Wang, F., Pan, Y. C., Elliston, K., Stern, D. and Shaw, A.
TITLE Cloning and expression of a cell surface receptor for advanced glycosylation end products of proteins
JOURNAL J. Biol. Chem. 267, 14998-15004 (1992)
MEDLINE 92340547
REFERENCE 2 (bases 1 to 1391)
AUTHORS Shaw, A.
TITLE Direct Submission
JOURNAL Submitted (15-APR-1992) A. Shaw, Department of Cellular and Molecular Biology, Merck Sharp and Dohme Research Laboratories, West Point, Pa. 19486 USA FEATURES Location/Qualifiers source 1..1391 /organism= "Homo sapiens" /db_xref="taxon:9606" /tissue_type="lung" CDS <1..1215 /standard_name= "RAGE" /codon_start=1 /product="receptor for advanced glycosylation end products" /protein_id= "AAA03574.1" /db_xref="GI:190846" /translation="

(SEQ ID NO: 3)
GAAGTAVGAWVLVLSLWGAVVGAQNITARIGEPLVLKCKGAPKKPPQRLE

WKLNTGRTEAWKVLSPQGGGPWDSVARVLPNGSLFLPAVGIQDEGIFRCR

-continued

AMNRNGKETKSNYRVRVYQIPGKPEIVDSASELTAGVPNKVGTCVSEGSY

PAGTLSWHLDGKPLVPNEKGVSVKEQTRRHPETGLFTLQSELMVTPARGG

DPRPTFSCSFSPGLPRHRALRTAPIQPRVWEPVPLEEVQLVVEPEGGAVA

PGGTVTLTCEVPAQPSPQIHWMKDGVPLPLPPSPVLILPEIGPQDQGTYS

CVATHSSHGPQESRAVSISIIEPGEEGPTAGSVGGSGLGTLALALGILGG

LGTAALLIGVILWQRRQRRGEERKAPENQEEEEERAELNQSEEPEAGESS

TGGP polyA_signal 1368.1373 polyA_site 1391
BASE COUNT 305 a 407 c 418 g 261 t

ORIGIN
```
   1 ggggcagccg aacagcagt tggagcctgg gtgctggtcc tcagtctgtg gggggcagta   (SEQ ID NO: 4)
  61 gtaggtgctc aaaacatcac agcccggatt ggcgagccac tggtgctgaa gtgtaagggg
 121 gcccccaaga aaccacccca gcggctgaa tggaaactga acacaggccg gacagaagct
 181 tggaaggtcc tgtctcccca gggaggaggc ccctgggaca gtgtggctcg tgtccttccc
 241 aacggctccc tcttccttcc ggctgtcggg atccaggatg aggggatttt ccggtgcagg
 301 gcaatgaaca ggaatggaaa ggagaccaag tccaactacc gagtccgtgt ctaccagatt
 361 cctgggaagc cagaaattgt agattctgcc tctgaactca cggctggtgt tcccaataag
 421 gtggggacat gtgtgtcaga gggaagctac cctgcaggga ctcttagctg gcacttggat
 481 gggaagcccc tggtgcctaa tgagaaggga gtatctgtga aggaacagac caggagacac
 541 cctgagacag ggctcttcac actgcagtcg gagctaatgg tgacccagc ccggggagga
 601 gatccccgtc ccaccttctc ctgtagcttc agcccaggcc ttccccgaca ccgggccttg
 661 cgcacagccc ccatccagcc ccgtgtctgg gagcctgtgc tctggagga ggtccaattg
 721 gtggtggagc cagaaggtgg agcagtagct cctggtggaa ccgtaaccct gacctgtgaa
 781 gtccctgccc agccctctcc tcaaatccac tggatgaagg atggtgtgcc cttgcccctt
 841 cccccagcc ctgtgctgat cctccctgag atagggcctc aggaccaggg aacctacagc
 901 tgtgtggcca cccattccag ccacgggccc caggaaagcc gtgctgtcag catcagcatc
 961 atcgaaccag gcgaggaggg gccaactgca ggctctgtgg gaggatcagg gctgggaact
1021 ctagccctgg ccctggggat cctgggaggc ctggggacag ccgccctgct cattgggggtc
1081 atcttgtggc aaaggcggca acgccgagga gaggagagga aggccccaga aaaccaggag
1141 gaagaggagg agcgtgcaga actgaatcag tcggaggaac ctgaggcagg cgagagtagt
1201 actggagggc cttgaggggc ccacagacag atcccatcca tcagctccct tttcttttc
1261 ccttgaactg ttctggcctc agaccaactc tctcctgtat aatctctctc ctgtataacc
1321 ccaccttgcc aagctttctt ctacaaccag agcccccac aatgatgatt aaacacctga
1381 cacatcttgc a//
```

LOCUS MUSRECEP 1348 by mRNA ROD 23-AUG-1994
DEFINITION Mouse receptor for advanced glycosylation end products (RAGE) gene, complete cds.
ACCESSION L33412VERSION L33412.1 GI:532208
KEYWORDS receptor for advanced glycosylation end products.
SOURCE *Mus musculus* (strain BALB/c, sub_species domesticus) (library: lambda gt10) male adult lung cDNA to mRNA.
ORGANISM *Mus musculus* Eukaryota; Metazoa; Chordata; Craniata; Vertebrata; Euteleostomi; Mammalia; Eutheria; Rodentia; Sciurognathi; Muridae; Murinae; *Mus*.
REFERENCE 1 (bases 1 to 1348)
AUTHORS Lundh, E. R., Morser, J., McClary, J. and Nagashima, M.
TITLE Isolation and characterization of cDNA encoding the murine and rat homologues of the mammalian receptor for advanced glycosylation end products
JOURNAL UnpublishedCOMMENT On Aug. 24, 1994 this sequence version replaced gi:496146.
FEATURES Location/Qualifiers source 1..1348/ organism="*Mus musculus*" /strain="BALB/c"/ sub_species="domesticus"/db_xref="taxon:10090"/ sex="male" /tissue_type="lung"/dev_stage="adult"/ tissue_lib="lambda gt10" gene 6.1217 /gene="RAGE" CDS 6.1217/gene="RAGE"/codon_start=1/product="receptor for advanced glycosylation end products"/ protein_id="AAA40040.1"/db_xref="GI:532209" /translation="

(SEQ ID NO: 5)
MPAGTAARAWVLVLALWGAVAGGQNITARIGEPLVLSCKGAPKKPPQQLE

WKLNTGRTEAWKVLSPQGGPWDSVAQILPNGSLLLPATGIVDEGTFRCRA

-continued

```
TNRRGKEVKSNYRVRVYQIPGKPEIVDPASELTASVPNKVGTCVSEGSYP

AGTLSWHLDGKLLIPDGKETLVKEETRRHPETGLFTLRSELTVIPTQGGT

THPTFSCSFSLGLPRRRPLNTAPIQLRVREPGPPEGIQLLVEPEGGIVAP

GGTVTLTCAISAQPPPQVHWIKDGAPLPLAPSPVLLLPEVGHADEGTYSC

VATHPSHGPQESPPVSIRVTETGDEGPAEGSVGESGLGTLALALGILGGL

GVVALLVGAILWRKRQPRREERKAPESQEDEEERAELNQSEEAEMPENGA

GGP
``` polyA_site 1333
BASE COUNT 301 a 394 c 404 g 249 t

```
ORIGIN
    1 gcaccatgcc agcggggaca gcagctagag cctgggtgct ggttcttgct ctatggggag    (SEQ ID NO: 6)

61 ctgtagctgg tggtcagaac atcacagccc ggattggaga gccacttgtg ctaagctgta 121 aggggggcccc taagaagccg ccccagcagc tagaatggaa actgaacaca ggaagaactg 181 aagcttggaa ggtcctctct ccccaggag gcccctggga cagcgtggct caaatcctcc 241 ccaatggttc cctcctcctt ccagccactg gaattgtcga tgaggggacg ttccggtgtc 301 gggcaactaa caggcgaggg aaggaggtca agtccaacta ccgagtccga gtctaccaga 361 ttcctgggaa gccagaaatt gtggatcctg cctctgaact cacagccagt gtccctaata 421 aggtggggac atgtgtgtct gagggaagct accctgcagg gacccttagc tggcacttag 481 atgggaaact tctgattccc gatggcaaag aaacactcgt gaaggaagag accaggagac 541 accctgagac gggactcttt acactgcggt cagagctgac agtgatcccc acccaaggag 601 gaaccaccca tcctaccttc tcctgcagtt tcagcctggg ccttccccgg cgcagacccc 661 tgaacacagc ccctatccaa ctccgagtca gggagcctgg gcctccagag ggcattcagc 721 tgttggttga gcctgaaggt ggaatagtcg ctcctggtgg gactgtgacc ttgacctgtg 781 ccatctctgc ccagccccct cctcaggtcc actggataaa ggatggtgca cccttgcccc 841 tggctcccag ccctgtgctg ctcctccctg aggtggggca cgcggatgag ggcacctata 901 gctgcgtggc cacccaccct agccacggac ctcaggaaag ccctcctgtc agcatcaggg 961 tcacagaaac cggcgatgag gggccagctg aaggctctgt gggtgagtct gggctgggta 1021 cgctagccct ggccttgggg atcctgggag gcctgggagt agtagccctg ctcgtcgggg 1081 ctatcctgtg gcgaaaacga caacccaggc gtgaggagag gaaggccccg gaaagccagg 1141 aggatgagga ggaacgtgca gagctgaatc agtcagagga gcggagatg ccagagaatg 1201 gtgccggggg accgtaagag cacccagatc gagcctgtgt gatggcccta gagcagctcc 1261 cccacattcc atcccaattc ctccttgagg cacttccttc tccaaccaga gcccacatga 1321 tccatgctga gtaaacattt gatacggc//
```

DEFINITIONS

"DNA sequence" is a linear sequence comprised of any combination of the four DNA monomers, i.e., nucleotides of adenine, guanine, cytosine and thymine, which codes for genetic information, such as a code for an amino acid, a promoter, a control or a gene product. A specific DNA sequence is one which has a known specific function, e.g., codes for a particular polypeptide, a particular genetic trait or affects the expression of a particular phenotype.

"Genotype" is the genetic constitution of an organism.

"Phenotype" is a collection of morphological, physiological and biochemical traits possessed by a cell or organism that results from the interaction of the genotype and the environment.

"Phenotypic expression" is the expression of the code of a DNA sequence or sequences which results in the production of a product, e.g., a polypeptide or protein, or alters the expression of the zygote's or the organisms natural phenotype.

"Zygote" is a diploid cell having the potential for development into a complete organism. The zygote can result from parthenogenesis, nuclear transplantation, the merger of two gametes by artificial or natural fertilization or any other method which creates a diploid cell having the potential for development into a complete organism. The origin of the zygote can be from either the plant or animal kingdom.

In the practice of any of the methods of the invention or preparation of any of the pharmaceutical compositions an "therapeutically effective amount" is an amount which is capable of alleviating the symptoms of the cognitive disorder of memory or learning in the subject. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

By "nervous system-specific" is meant that expression of a nucleic acid sequence occurs substantially in a nervous system tissue (for example, the brain or spinal cord).

Preferably, the expression of the nucleic acid sequence in the nervous system tissue represents at least a 5-fold, more preferably, a 10-fold, and, most preferably, a 100-fold increase over expression in non-nervous system tissue.

The "non-human animals" of the invention include vertebrates such as rodents, non-human primates, sheep, dog, cow, amphibians, reptiles, etc. Preferred non-human animals are selected from the rodent family including rat and mouse, most preferably mouse.

The "transgenic non-human animals" of the invention are produced by introducing "transgenes" into the germline of the non-human animal.

ADVANTAGES OF THE PRESENT INVENTION

The transgenic non-human mammals of the present invention will provide insights with respect to how and where protein interactions occur in Alzheimer's Disease and thus provide more useful models for testing the efficacy of certain drugs in preventing or reducing the onset or progression of this disease. The transgenic non-human mammals of the present invention include recombinant genetic material comprised of a nucleic acid sequence encoding RAGE fused to specific promoters capable of expressing the protein in specific tissues such as nerve tissues generally and/or specific types of nerve tissue, e.g., the brain.

As described herein, the current invention provides a number of advantages. First, because transgenic animals are generally useful for the investigation of specific biological processes and for reproducing particular aspects of human disease, the transgenic animals of the invention provide an important, reproducible and accurate means for screening drugs to isolate therapeutic agents. In particular, the transgenic animals that are described for the first time herein have the advantage of mimicking the defects observed in patients with Alzheimer's disease. Accordingly, the efficacy of a particular therapy may be examined in the same animal at different disease stages. Importantly, because this invention provides a transgenic animal model of Alzheimer's disease with measurable phenotypes, compounds may be screened to identify those which alleviate this symptom, even absent knowledge of the symptom's underlying biological cause.

In addition, although not strictly required for drug screening, the associated neuro-pathological symptoms exhibited by the transgenic animal models described herein provide the unique advantage of allowing the investigation of the etiology of Alzheimer's disease. For example, the appearance of reduced synaptic plasticity or the reduced basal synaptic transmission may be correlated with the appearance of specific behavioral impairments within individuals or groups of animals. In addition, treatments which are shown to improve memory function may be tested for their ability to selectively improve certain pathological symptoms.

Another advantage of this invention is the ease with which these transgenic animals are bred to produce identical transgenic progeny. The animals of the invention may be generated in sufficient quantity to make them widely and rapidly available to researchers in this field.

FURTHER DETAILED DESCRIPTION OF THE INVENTION

The present invention also provides for a transgenic non-human animal whose germ or somatic cells contain a nucleic acid molecule which comprises: (a) a neuronal tissue specific promoter operatively linked to a DNA sequence encoding a receptor for advanced glycation endproduct (RAGE), introduced into the mammal, or an ancestor thereof, at an embryonic stage.

This transgenic animal may be used in screening methods for compounds which would be useful in the treatment of neurological disorders in humans method for screening compounds for their potential use as therapeutic agents which comprises administering to the transgenic non-human mammal described herein the compound, in various amounts, and observing whether the neurological function of the transgenic mammal improves or not (as determined by, for example, basal synaptic transmission, synaptic plasticity, neuronal stress, et al.).

The neurological disorder may be amnesia, Alzheimer's disease, amyotrophic lateral sclerosis, a brain injury, cerebral senility, chronic peripheral neuropathy, a cognitive disability, a degenerative disorder associated with learning, Down's Syndrome, dyslexia, electric shock induced amnesia or amnesia. Guillain-Barre syndrome, head trauma, Huntington's disease, a learning disability, a memory deficiency, memory loss, a mental illness, mental retardation, memory or cognitive dysfunction, multi-infarct dementia and senile dementia, myasthenia gravis, a neuromuscular disorder, Parkinson's disease, Pick's disease, a reduction in spatial memory retention, senility, or Turret's syndrome.

The compound which is tested in the screening method of the present invention may be an organic compound, a nucleic acid, a small molecule, an inorganic compound, a lipid, or a synthetic compound. The mammal may be a mouse, a sheep, a bovine, a canine, a porcine, or a primate. The administration may comprise intralesional, intraperitoneal, intramuscular or intravenous injection; infusion; liposome-mediated delivery; gene bombardment; topical, nasal, oral, anal, ocular or otic delivery.

The present invention also provides for a method for alleviating symptoms in a subject suffering from a neurological disorder which comprises administering to the subject an effective amount of the compound evaluated by the methods hereinabove in an amount effective to treat the symptoms in the subject suffering from a neurological disorder.

The administration may be intralesional, intraperitoneal, intramuscular or intravenous injection; infusion; liposome-mediated delivery; gene bombardment; topical, nasal, oral, anal, ocular or otic delivery.

Pharmaceutical Compositions and Carriers

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of protein compositions and compounds together with suitable diluents, preservatives, solubilizers, emulsifiers, adjuvants and/or carriers useful in treatment of neuronal degradation due to aging, a learning disability, or a neurological disorder. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the compound of the invention may be "labeled" by association with a detectable marker substance (e.g., radiolabeled with $^{125}$I or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment the compound of the present invention is associated with a pharmaceutical carrier which includes a pharmaceutical composition. The pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

Transgenic Technology and Methods

The following U.S. patents are hereby incorporated by reference: U.S. Pat. No. 6,025,539, IL-5 transgenic mouse; U.S. Pat. No. 6,023,010, Transgenic non-human animals depleted in a mature lymphocytic cell-type; U.S. Pat. No. 6,018,098, In vivo and in vitro model of cutaneous photoaging; U.S. Pat. No. 6,018,097, Transgenic mice expressing human insulin; U.S. Pat. No. 6,008,434, Growth differentiation factor-11 transgenic mice; U.S. Pat. No. 6,002,066; H2-M modified transgenic mice; U.S. Pat. No. 5,994,618, Growth differentiation factor-8 transgenic mice; U.S. Pat. No. 5,986,171, Method for examining neurovirulence of polio virus, U.S. Pat. No. 5,981,830, Knockout mice and their progeny with a disrupted hepsin gene; U.S. Pat. No. 5,981, 829, .DELTA.Nur77 transgenic mouse; U.S. Pat. No. 5,936, 138; Gene encoding mutant L3T4 protein which facilitates HIV infection and transgenic mouse expressing such protein; U.S. Pat. No. 5,912,411, Mice transgenic for a tetracycline-inducible transcriptional activator; U.S. Pat. No. 5,894,078, Transgenic mouse expressing C-100 app.

The methods used for generating transgenic mice are well known to one of skill in the art. For example, one may use the manual entitled "Manipulating the Mouse Embryo" by Brigid Hogan et al. (Ed. Cold Spring Harbor Laboratory) 1986.

See for example, Leder and Stewart, U.S. Pat. No. 4,736,866 for methods for the production of a transgenic mouse.

For sometime it has been known that it is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include the genotype of the exogenous genetic material. Additionally, the inclusion of exogenous genetic material in the zygote will result in a phenotype expression of the exogenous genetic material.

The genotype of the exogenous genetic material is expressed upon the cellular division of the zygote. However, the phenotype expression, e.g., the production of a protein product or products of the exogenous genetic material, or alterations of the zygote's or organism's natural phenotype, will occur at that point of the zygote's or organism's development during which the particular exogenous genetic material is active. Alterations of the expression of the phenotype include an enhancement or diminution in the expression of a phenotype or an alteration in the promotion and/or control of a phenotype, including the addition of a new promoter and/or controller or supplementation of an existing promoter and/or controller of the phenotype.

The genetic transformation of various types of organisms is disclosed and described in detail in U.S. Pat. No. 4,873,191, issued Oct. 10, 1989, which is incorporated herein by reference to disclose methods of producing transgenic organisms. The genetic transformation of organisms can be used as an in vivo analysis of gene expression during differentiation and in the elimination or diminution of genetic diseases by either gene therapy or by using a transgenic non-human mammal as a model system of a human disease. This model system can be used to test putative drugs for their potential therapeutic value in humans.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote. The zygote is allowed to develop into an organism such as by implanting it in a pseudopregnant female. The resulting organism is analyzed for the integration of the exogenous genetic material. If positive integration is determined, the organism, can be used for the in vivo analysis of the gene expression, which expression is believed to be related to a particular genetic disease.

Attempts have been made to study a number of different types of genetic diseases utilizing such transgenic animals. Attempts related to studying Alzheimer's disease are disclosed within published PCT application WO89/06689 and PCT application WO89/06693, both published on Jul. 27, 1989, which published applications are incorporated herein by reference to disclose genetic sequences coding for Alzheimer's .beta.-amyloid protein and the incorporation of such sequences into the genome of transgenic animals.

Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster, et al. (1985) Proc. Natl. Acad. Sci. U.S.A. 82, 4438-4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) Proc. Natl. Acad. Sci U.S.A. 73, 1260-1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al. (1985) Proc. Natl. Acad. Sci. U.S.A. 82, 6927-6931; Van der Putten, et al. (1985) Proc. Natl. Acad. Sci U.S.A. 82, 6148-6152). Transfection is easily and efficiently obtained by culturing the blastomeres on a monolayer of virus-producing cells (Van der Putten, supra; Stewart, et al. (1987) EMBO J. 6, 383-388). Alternatively, infection can be performed at a later stage. Virus or virus-producing cells can be injected into the blastocoele (Jahner, D., et al. (1982) Nature 298, 623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, D. et al. (1982) supra).

A third type of target cell for transgene introduction is the embryonal stem cell (ES). ES cells are obtained from pre-implantation embryos cultured in vitro and fused with embryos (Evans, M. J., et al. (1981) Nature 292, 154-156; Bradley, M. O., et al. (1984) Nature 309, 255-258; Gossler, et al. (1986) Proc. Natl. Acad. Sci U.S.A. 83, 9065-9069; and Robertson, et al. (1986) Nature 322, 445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468-1474.

As used herein, a "transgene" is a DNA sequence introduced into the germline of a non-human animal by way of human intervention such as by way of the above described methods.

The disclosures of publications referenced in this application in their entireties are hereby incorporated by reference into this application in order to more fully describe the state of the art as known to those skilled therein as of the date of the invention described and claimed herein.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Generation of Transgenic Mice with Targeted Overexpression of Receptor for Advanced Glycation Endproducts (RAGE) in Neurons This paper describes a means of making transgenic mice with targeted overexpression of RAGE in neurons using the PDGF B-chain promoter and the cDNA for human full-length RAGE. The mice, termed Tg PD-RAGE, which have been produced provide a model system for determining the consequences of heightened RAGE expression in neurons, and could serve as an important model system to test RAGE blockers, either inhibitors of ligand-receptor interaction or inhibitors of RAGE-dependent intracellular signalling. Cross-breeding of Tg PD-RAGE with other animals, such as those expressing a transgene causing overexpression of mutant amyloid precursor protein (resulting in increased production of amyloid-beta peptide) provide a model system to assess the effects of RAGE in an Aβ-rich environment in the brain relevant to Alzheimer's disease. In addition, isolation and culture of embryonic neurons from Tg PD-RAGE mice allows study of the consequences of increased levels of RAGE in vitro in actual neurons. These are several examples of how Tg PD-RAGE mice can be used to assess the contribution of RAGE, analyzed according to in vitro and in vivo systems, to situations potentially relevant to human disease.

Introduction

Receptor for Advanced Glycation Endproducts (RAGE) is a multiligand member of the immunoglobulin superfamily of cell surface molecules[1]. In the central nervous system, RAGE is present at high levels in early development, but then its expression falls off with maturity[2,3]. However, with development of a pathology in the central nervous system, such as Alzheimer's disease (AD), RAGE expression increases to high levels[4]. Similarly, in murine models of stroke RAGE expression also increases. This suggests that RAGE may participate in the host response, though it is not clear if its participation would be favorable or deleterious to the outcome.

There are several ways to dissect the contribution of RAGE in physiologic and pathophysiologic settings. One method which we have used extensively is administration of soluble RAGE, the extracellular domain, which serve as a decoy for ligands seeking out cell surface receptor, and anti-RAGE IgG[5-7]. However these reagents are principally useful in tissues served by the systemic circulation which provides the means for delivery. Tissues behind the blood-brain barrier, such as neurons (e.g., the entire central nervous-system) pose a more difficult problem since macromolecules do not have ready access under most conditions. For this reason, we sought to create genetic models to dissect the contribution of RAGE. In this context, there are three general approaches:

Targeted over-expression of wild-type RAGE wherein the transgenic non-human animal would exhibit exaggerated effects of RAGE in the particular tissue/cell under study (the RAGE is overexpressed in a tissue specific manner.

Targeted overexpression of a mutant form of the receptor in which the RAGE cytosolic tail has been deleted. This form of the molecule functions as a dominant-negative, thereby blocking the effects of ligand engagement of wild-type RAGE.

Deletion of the RAGE gene by homologous recombination (this can also be carried out using conditional strategies to achieve tissue-specific knockout. (Also termed, a RAGE knockout transgenic non-human animal.)

This report describes the generation of mice with targeted overexpression of human RAGE in neurons using the PDGF B-chain promoter, termed Tg PD-RAGE mice. In addition, we describe the effect of stroke on Tg PD-RAGE mice, and the results of crossing Tg PD-RAGE mice with animals overexpressing a mutant form of amyloid precursor protein (APP) which causes increased production of amyloid-beta peptide (Aβ).

Methods

Construction of the transgene and making the transgenic (Tg) mice. The platelet-derived growth factor (PDGF) B-chain.

promoter was used to drive overexpression of RAGE in neurons of the central nervous system of transgenic (Tg) mice[8]. Transgene constructs were prepared using a previously described vector[9,10]. Briefly, the CMV, immediate/early promoter was excised from the commercial expression vector pCI (Promega, Madison Wis.), and replaced with an oligonucleotide polylinker. The PDGF B-chain promoter fragment was mobilized as an XbaI fragment[8] and cloned into a unique SpeI site designed within the synthetic linker. The full-length human RAGE cDNA was inserted into the NotI site of the original polylinker. A schematic representation of this construct is shown in FIG. 1A (upper panel). An ~3 kb fragment containing the promoter, cDNA and required other sequences was then excised from the plasmid backbone as a PvuI fragment (FIG. 1B, lower panel) and microinjected mouse B6CBAF$_1$/J oocytes. The latter were implanted into pseudopregnant females and mated with B6CBAF$_1$/J males resulting in the generation of independent founders. Breeding of these mice demonstrated germ-line transmission and was used to produce lines of animals termed Tg PD-RAGE.

Founders were initially identified by Southern blotting performed on DNA extracted from mouse tails. DNA was digested, run on agarose gels, and hybridized with $^{32}$P-labelled cDNA for human RAGE. Tails were digested with proteinase K (500 µg/ml) in digestion buffer (50 mM Tris, pH 8.0, 100 mM EDTA, 0.5% SDS) at 55° C. for overnight. Then, purified DNA was cleaved with EcoRI overnight at 37° C. Labelling of the probe was done using the Stratagene's Probe Labeling Kit™. Autoradiography was then performed.

Subsequent screening of progeny was by PCR using the following primers: 5'-AGCGGCTGGAATGGAAACT-GAACA-3' (SEQ ID NO:7) and 3'-GAAGGGGCAAGGGCACACCATC-5' (SEQ ID NO:8). Total RNA was isolated using Trizol®, and RT-PCR was performed with the following thermocycling parameters: 30 sec for each cycle consisting of incubations at 95° C. for 20 sec, 57° C. for 30 sec and 72° C. for 1 sec for a total of 35 cycles. Products were analyzed by agarose gel electrophoresis and visualized by ethidium bromide staining under ultraviolet illumination. The size of the RAGE amplicon with these primers corresponded to 701 bp.

Northern and immunoblotting utilized the same procedures as above, except that tissue was homogenized in the presence of Trizol (RNA) or in homogenization buffer (Tris/HCl, 10 mM, pH 7.4; NaCl, 100 mM; phenylmethylsulfonylfluoride, 100 µg/ml; EDTA, 1 mM; aprotonin, 1 µg/ml). Note that immunoblotting and immunostaining of brain tissue from Tg PD-ABAD mice used anti-human RAGE IgG[7].

Characterization of RAGE expression in Tg PD-RAGE mice. Northern analysis was performed on total RNA isolated from cerebral cortex, hippocampus and cerebellum. RNA was isolated using Trizol® followed by electrophoresis on 0.8% agarose gels (30 µg was applied to each lane), transfer to nitrocellulose membranes, and hybridization with $^{32}$P-labelled human RAGE cDNA. The RAGE cDNA was labelled by as above.

Western blotting was performed on protein extracts of brain subregions. Proteins were extracted from minced pieces of brains by exposing the tissue to lysis buffer (Tris/HCl, 20 mM; pH 7.4; Triton X-100, 1%; phenylmethylsulfonylfluoride, 2 mM; EDTA, 1 mM, aprotonin, 10 μg/ml; leupeptin, 10 μg/ml) using a ratio of 1 ml of buffer per 0.5 gm of tissue. Extracts were then boiled in reducing SDS-sample buffer, and applied to SDS-PAGE according to Laemmli[11].

Immunostaining was performed on paraformaldehyde (4%)-fixed, paraffin embedded sections (6 μm) of mouse brains prepared according to standard methods[4,7]. The sections were deparaffinized and dehydrated, and then stained with rabbit anti-human RAGE IgG (50 μg/ml) followed by goat anti-rabbit biotin-conjugated IgG and ExtrAvidin-conjugated with alkaline phosphatase (Biotin ExtrAvidin® kit; Sigma, St. Louis Mo.). Preparation of Anti-Rage IgG, Using Recombinant Soluble Rage as the immunogen, has been described[4,7].

Induction of stroke in Tg PD-RAGE mice. Functional consequences of overexpression of RAGE were first assessed in response to ischemic stress, the transient middle cerebral artery occlusion model. Murine stroke model Mice (C57BL6/J, male) were subjected to stroke according to previously published procedures[12]. Following anesthesia, the carotid artery was accessed using the operative approach previously described in detail[13], including division/coagulation of the occipital and pterygopalatine arteries to obtain improved visualization and vascular access. A nylon suture was then introduced into the common carotid artery, and threaded up the internal carotid artery to occlude the origin of the right middle cerebral artery (MCA). Nylon (polyamide) suture material was obtained from United States Surgical Corporation (Norwalk, Conn.), and consisted of 5.0 nylon/13 mm length for 27-36 g mice, and 6.0 nylon/12 mm length for 22-26 g mice. After 45 minutes of occlusion, the suture was withdrawn to achieve a reperfused model of stroke. Although no vessels were tied off after the suture was removed, the external carotid arterial stump was cauterized to prevent frank hemorrhage.

Measurements of relative cerebral blood flow were obtained as previously reported[12-15] using a straight laser doppler flow probe placed 2 mm posterior to the bregma, and 6 mm to each side of midline using a stereotactic micromanipulator, keeping the angle of the probe perpendicular to the cortical surface. These cerebral blood flow measurements, expressed as the ratio of ipsilateral to contralateral blood flow, were obtained at baseline, and immediately prior to MCA occlusion, 45 minutes after MCA occlusion, and at several time points after withdrawal of the occluding suture.

Measurement of Cerebral Infarction Volumes: After 24 hours, animals were euthanized and their brains rapidly harvested. Infarct volumes were determined by staining serial cerebral sections with triphenyl tetrazolium chloride and performing computer-based planimetry of the negatively (infarcted) staining areas to calculate infarct volume (using NIH image software).

Neurological Exam: Prior to giving anesthesia, mice were examined for neurological deficit 23 h after reperfusion using a four-tiered grading system: a score of 1 was given if the animal demonstrated normal spontaneous movements; a score of 2 was given if the animal was noted to be turning towards the ipsilateral side; a score of 3 was given if the animal was observed to spin longitudinally (clockwise when viewed from the tail); and, a score of 4 was given if the animal was unresponsive to noxious stimuli. This scoring system has been previously described in mice[12-14], and is based upon similar scoring systems used in rats[16]. Immunostaining of cerebral cortex following induction of stroke in wild-type mice was performed as described above using a rabbit polyclonal antibody made using purified recombinant murine ABAD as the immunogen. Quantitation of microscopic images was accomplished with the Universal Imaging System.

Cross-breeding of Tg PD-RAGE mice with Tg hAPP mice. Tg mice overexpressing an alternatively spliced hAPP minigene that encodes hAPP695, hAPP751, and hAPP770 bearing mutations linked to familial AD (V717F, K670M/N671L) have been produced by Dr. Lennart Mucke[17], and provided to us for use in cross-breeding studies with Tg PD-RAGE mice. In these mice, expression of the transgene is also driven by the PDGF B-chain promoter. Cross-breeding was performed and double-transgenic mice expressing both hAPP and PD-RAGE transgenes were identified with specific primers. The primers for the hAPP transgene were: 5'-GACAAG-TATCTCGAGACACCTGGGGATGAG-3' (SEQ ID NO:9) and 3'-AAAGAACTTGTAGGTTGGATTTTCGTACC-5' (SEQ ID NO:10). PCR conditions for the amplifying the hAPP transgene were the same as those described above, and the size of the amplicon was 1169 bp.

Characterization of Tg PD-RAGE/hAPP mice. Mice were anesthetized according to standard procedures and then flush-perfused transcardially with solution containing NaCl (0.9%). Brains will then be rapidly removed and divided sagitally. One hemibrain was postfixed in phosphate-buffered saline (PBS) containing paraformaldehyde (4%; pH 7.4) at 4° C. for 48 hrs prior to vibratome sectioning. Hemibrains were stored in cryoprotectant medium (phosphate-buffered saline containing glycerin and ethylene glycol) until sectioning. This portion of the brain was employed for studies of neuronal integrity and degeneration. There is ample evidence that loss of synaptophysin immunoreactivity in presynaptic terminals is associated with AD brain, a marker which correlates with extent of cognitive impairments[18-23]. Additionally, immunoreactivity for Microtubule-associated protein (MAP)-2 was examined as a marker of neuronal cell bodies and dendrites, as a significant decrease of MAP-2 immunoreactive dendrites has been observed for example, in brains of patients with neurodegeneration subsequent to HIV-1 encephalitis[24].

Hemibrains were subjected to sagittal sectioning employing a Leica Vibratome® 1000E. Sections, 40 μm thick, were prepared and collected into the wells of 12-well tissue culture plates in cryoprotectant medium and stored at −20° C. until immunostaining was performed. Two sections per mouse were randomly selected for further study, based on full integrity of the sample, i.e., clearly delineated neocortex, and CA1, CA2 and CA3 were completely intact. Prior to immunohistochemistry, free-floating sections were placed individually in wells of 24-well tissue culture plates and washed twice in phosphate-buffered saline (PBS; pH 7.4; containing calcium/magnesium). Sections were then permeabilized in PBS containing Triton X-100 (0.2) for 20 min at room temperature. Sections were stained with antibodies to perform assessment of neuronal integrity. Anti-synaptophysin IgG (Boehringer) was employed as a marker of presynaptic terminals. Anti-MAP-2 IgG (Boehringer) was employed as a marker of neuronal cell bodies/dendrites. The appropriate nonimmune IgG was employed as a control (Boehringer Mannheim). After appropriate blocking steps, primary antibodies were incubated with sections and then washed in PBS. FITC-labeled secondary antibodies (Vector system; ABC) were employed to visualize sites of primary antibody binding. After washing, sections were mounted using Vectashield on glass slides and then coverslips placed atop the sections. Sections will then be kept in the dark at 4° C., for no more than two weeks prior to analysis.

Semiquantitative evaluation of neuronal integrity was performed using laser scanning confocal microscopy. Neuronal integrity was assessed in the neocortex and pyramidal cell layer of the hippocampus (CA1 subfield) in six sections per mouse (two for each antibody marker). For each mouse, 4-8 confocal images (3-4/section) of the neocortex, and 2-4 confocal images (1-2/section) of the hippocampal CA1 subfield, each covering an area of 210×140 µm, were obtained. Under 60×, oil immersion, the sample was focused and iris and gain levels adjusted to obtain images with a pixel intensity within a linear range. Each final image was processed sequentially in Lasersharp. Digitized images were then transferred to a Macintosh computer using Adobe Photoshop, JPEG compression and analyzed with NIH Image. The area of the neuropil occupied by MAP-2-labeled dendrites or by synaptophysin-labeled presynaptic terminals was quantified and expressed as a percentage of the total image area as described[24]. Final analysis of digitized images for area neuropil occupied was determined by two independent investigators. Mean±standard deviation is reported for each section. Control sections were studied under conditions in which primary antibody was omitted, and no signal was observed with secondary antibody alone.

Immunostaining of mouse brain for other markers employed commercially available goat antibody to murine macrophage-colony stimulating factor (goat anti-M-CSF IgG; 10 µg/ml; Santa Cruz), rabbit antibody to activated caspase 3 (50 µg/ml; PharMingen), and mouse monoclonal antibody to phosphorylated tau (AT8; 10 µg/ml; Immunogenetics). In each case, the immunostaining protocol used standard techniques according to the manufacturer's instructions. Rabbit anti-murine Interleukin (IL) 6 IgG was provided by Dr. Gerald Fuller (University of Alabama Medical Center, Birmingham) and has been used in previous studies[25]. Sections were incubated with primary antibodies overnight at 4° C., followed by blocking with appropriate antisera and addition of biotin-conjugated goat anti-rabbit, goat anti-mouse or mouse anti-goat IgG (1:25 dilution) for 30 min at 37° C. Then ExtrAvidin® conjugated to peroxidase or to alkaline phosphatase (1:25 dilution) was added for 25 min at 37° C. Slides were then washed and developed with 3-amino-9-ethyl carbazole or fast red. Sections were viewed in an Olympus microscope, and images were quantified using the Universal imaging system.

Activation of the transcription factor NF-kB was studied in brains of mice and in neurons cultured from this tissue (see below). Nuclear extracts were prepared according to the method of Dignam et al.[26], and were incubated with $^{32}$P-labelled double stranded consensus oligonucleotide probe for NF-kB (Santa Cruz) followed by polyacrylamide gel electrophoresis and autoradiography. These methods have been described previously using brain tissue and cultured cells as the samples for preparation of nuclear extracts[4].

Isolation and characterization of neurons from Tg PD-RAGE mice. Brains of E16-18 mouse embryos were processed by a modification of a previously described method[27]. In brief, Embryos were washed in ethanol (75%), transferred to a dish with sterile phosphate-buffered saline (PBS) at 4° C. under a tissue culture hood. Two embryos were dissected at a time immersed in Neurobasal Medium (GIBCO) with NaCl (22 mM), $NaHCO_3$ (4.4 mM), penicillin (50 units/ml) and streptomycin (50 µg/ml). The embryo tail was removed and analyzed by PCR to determine genotype (as above). Cerebral cortex was dissected free from the cerebellum and brainstem, sliced into 1 mm pieces, and transferred to 1.5 ml eppendorf tubes in the above medium. The tube was centrifuged at 400 rpm, the pellet was washed in PBS, and resuspended in PBS. Then, trypsin (0.25%; 0.5 ml) and DNAse (250 units/ml) were added and the incubation was continued for 15 min at 37° C. with gentle shaking. The mixture was decanted, washed twice in PBS by inverting the tube and gently spinning at 400 rpm for 5 min. Neurons were cultured in growth medium (Neurobasal Medium with B27, 2%, L-glutamine, 2 mM, penicillin, 50 units/ml, streptomycin, 50 µg/ml) in wells coated with poly-L-lysine. Neurons were identified immunocytochemically using antibody to neurofilament (Sigma) and the methods for immunostaining described above.

Cultures of neurons were exposed to preformed Aβ(1-42) fibrils for 5 hrs at 37° C. Aβ(1-42) synthetic peptide was purchased from QCB, and was incubated for 5 days at 37° C. to allow fibril formation to occur. The presence of fibrils was confirmed by electron microscopy. Fibril preparations were then frozen (−20° C.) until use. Just prior to an experiment, fibril preparations were thawed, vortexed, and then added to culture medium to a final concentration of 0.5 µM for 5 hrs (NF-kB activation) or 30-40 hrs (detection of activated caspase 3) at 37°. Nuclear extracts were prepared and EMSA was performed as above. Where indicated, anti-RAGE IgG was added during incubation of Aβ fibrils with the cells.

Caspase 3 activity was studied using a kit from Clontech.

Results

Figure 3:
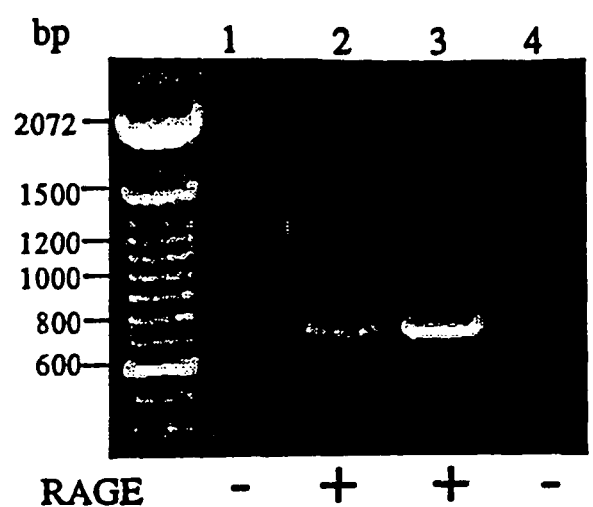
FIG. 3. Identification of Tg PD-RAGE mice (+) and nontransgenic littermate controls (-) by PCR.

Identification of Tg PD-RAGE mice. Southern analysis identifying three Tg PD-RAGE founders is shown in FIG. 2. These mice were used to generate lines of Tg PD-RAGE mice in whom the progeny were identified by PCR using the primers described in the methods section. An example of PCR detection of positive founders, versus negative non-Tg animals is shown in FIG. 3.

Figure 4:
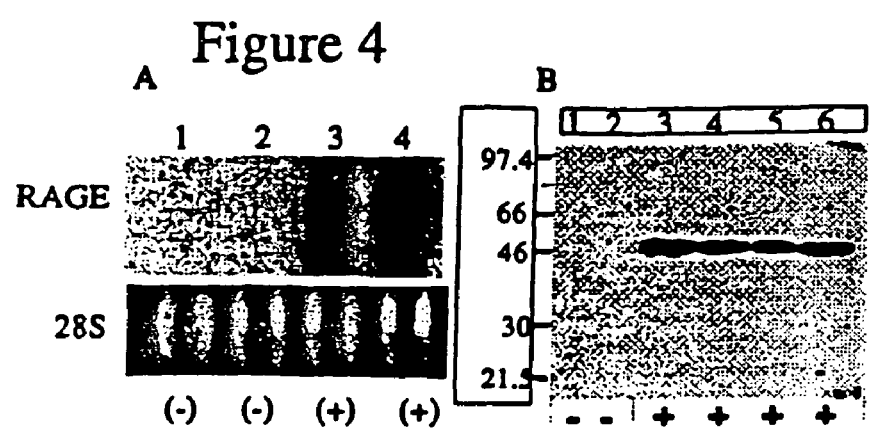
Figure 5:
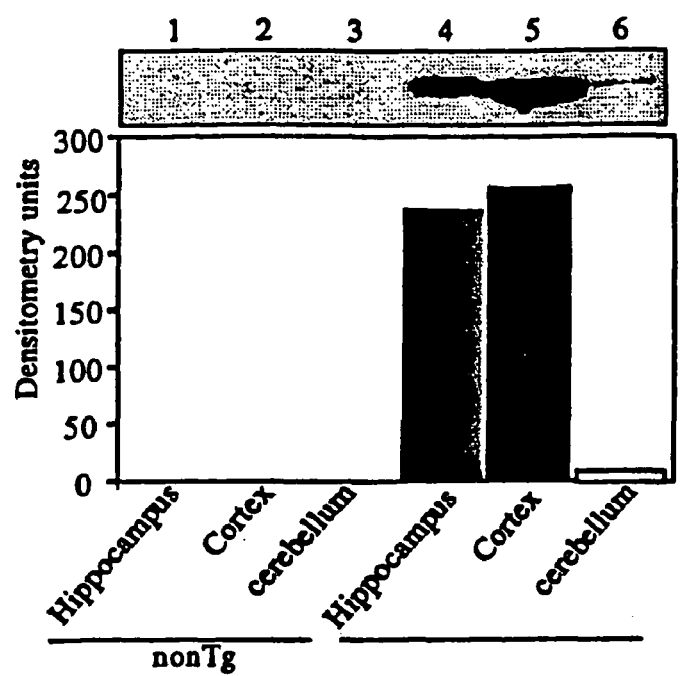
FIG. 5. RAGE expression in brain subregions of Tg PD-RAGE mice compared with nontransgenic littermate controls (nonTg). Immunoblotting was performed protein extracts of brain homogenates derived from the indicated brain subregion.

Characterization of Tg PD-RAGE mice. Expression of the transgene in the brain was determined by Northern analysis of total RNA extracted from cerebral cortex with $^{32}$P-labelled cDNA for human RAGE (FIG. 4A). An intense band was observed in Tg PD-RAGE mice, but not in nontransgenic littermate controls. Similarly Western analysis was performed on protein extracts of cerebral cortex from transgenic mice using antibody to the extracellular domain of recombinant human RAGE. Again, a strong band of immunoreactivity migrating above the 46 kDa molecular weight marker confirmed the presence of high levels of RAGE antigen in brains of Tg PD-RAGE mice compared with nontransgenic littermate controls (FIG. 4B). Immunoblotting was then performed on brain subregions, including cerebral cortex, hippocampus and cerebellum, with anti-RAGE IgG (FIG. 5). In Tg PD-RAGE mice, intense immunoreactive bands were seen in cerebral cortex and hippocampus, compared with lower levels of transgene expression in the cerebellum. Immunostaining with anti-RAGE IgG confirmed that the increased levels of RAGE in Tg PD-RAGE animals were in neurons (FIGS. 6A-B). These data indicate that Tg PD-RAGE mice provide a model system in which neurons of the brain, especially cerebral cortex and hippocampus express high levels of RAGE.

Figure 7:
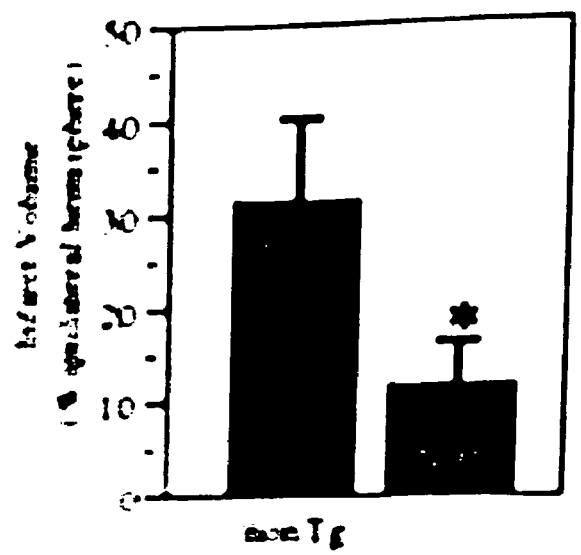
FIG. 7. Transient middle cerebral artery occlusion model of stroke in mice: comparison of infarct volume in Tg PD-RAGE and nontransgenic littermate controls (nonTg). *P<0.05.

To examine consequences of enhanced neuronal RAGE expression for ischemic stress experiments were performed in a murine model of transient occlusion of the middle cerebral artery (FIG. 7). Tg PD-RAGE mice, as well as nonTg littermate controls weighed ≈126 grams and were ≈10 wks old. Neurologic deficit score, evaluated at the 24 hr point, was reduced in Tg PD-RAGE mice compared with nonTg littermates. The volume of infarcted cerebral tissue was reduced by ~50% in Tg mice (FIG. 7; $p<0.05$).

Characterization of Tg PD-RAGE/hAPP mice. The increased expression of RAGE in brain, compared with age-matched non-demented brain, suggested that the receptor might be associated with AD pathology. Consistent with this hypothesis, our pilot studies with Tg hAPP mice displayed increased levels of RAGE in cerebral cortex by 4 months of age, which is prior to plaque formation. Tg hAPP mice are especially useful for studies to assess the effect of introduction of the PD-RAGE transgene since they have been characterized in previous studies with respect to neuropathologic and electrophysiologic properties.

Figure 8:
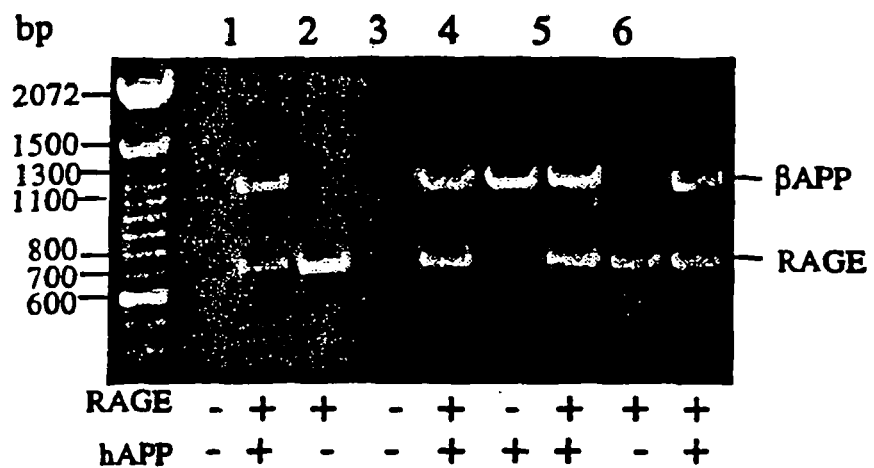
FIG. 8. Identification of double transgenic mice overexpressing RAGE and mutant human APP by PCR.

If RAGE-Aβ interaction promoted neuronal stress, we reasoned that expression of high levels of RAGE at early times in the brains of animals expressing the hAPP transgene might result in magnified cell stress and cytotoxicity (the transgenic model introduces higher levels of RAGE expression than were present in Tg hAPP mice alone, and thus, potentially represents a model of exaggerated effects of RAGE due to overexpression of the receptor). Cross-breeding studies were performed and double transgenic mice were identified by PCR using primers specific for the PD-RAGE transgene and the hAPP transgene. Results of a representative PCR analysis are shown in FIG. 8 demonstrating amplicons for both the PD-RAGE and hAPP genes in the double-transgenic animals versus single transgenics and nontransgenic littermate controls. The double transgenic mice have been termed Tg PD-RAGE/hAPP mice.

Figure 9:
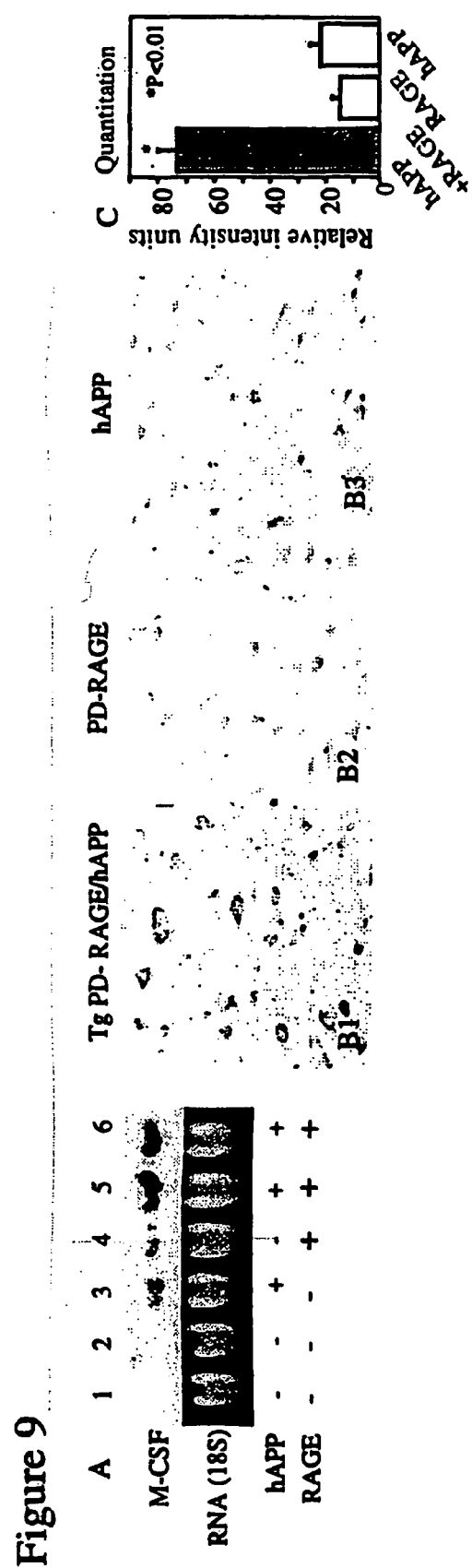
Figure 10:
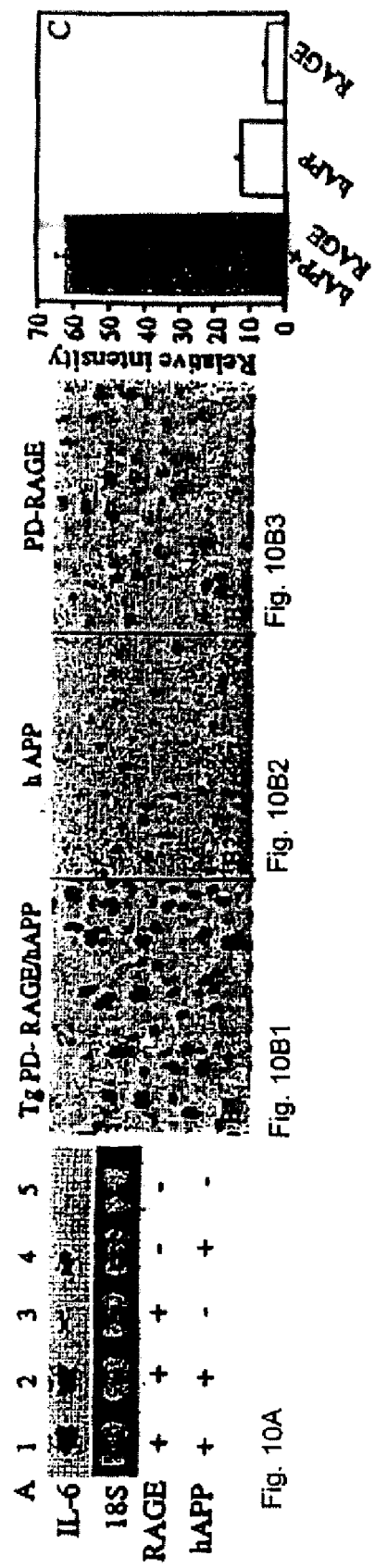
Figure 11:
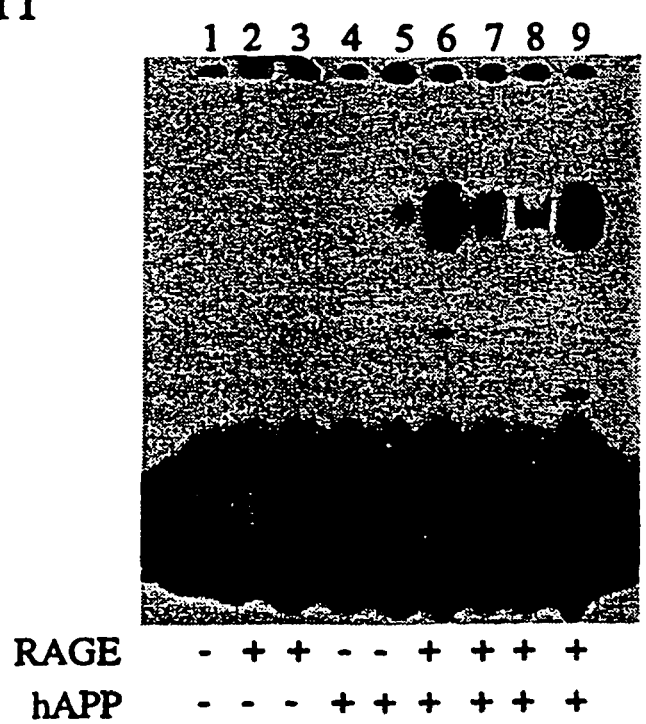
FIG. 11. EMSA for NF-kB on nuclear extracts from cerebral cortex of mice overexpressing RAGE (2,3), mutant human APP (hAPP; 4,5), both transgenes (6-9), and nontransgenic littermate control (1).

Double transgenic mice were observed for three-four months and evidence of neuronal stress was then analyzed by studying expression of M-CSF (FIGS. 9A, 9B1-B3, 9C) and IL-6 (FIGS. 10A, 10B1-B3, 10C), and activation of NF-kB (FIG. 11). Northern analysis of cerebral cortex showed increased levels of transcripts for M-CSF in Tg PD-RAGE/hAPP mice compared with single transgenics (Tg hAPP and Tg PD-RAGE) and nonTg littermate controls (FIG. 9A). Immunostaining with anti-M-CSF IgG confirmed that the increase in M-CSF antigen was predominately in neurons, and that double-transgenics showed elevated levels of antigen compared with the other groups (FIG. 9B1, 9B2, 9B3 and 9C). Similar results were observed with respect to increased expression of IL-6 transcripts and antigen (FIG. 10A, 10B1-B3, 10C)). Since activation of NF-kB is associated with cellular stress responses and can underlie expression of M-CSF and IL-6, we analyzed nuclear translocation of NF-kB in nuclear extracts prepared from brains of the transgenic mice by EMSA (FIG. 11). Analysis of double transgenic mice invariably displayed a strong gel shift band, whose intensity varied somewhat in the different animals, whereas weak/absent bands were seen in the control group and single transgenics.

Figure 12:
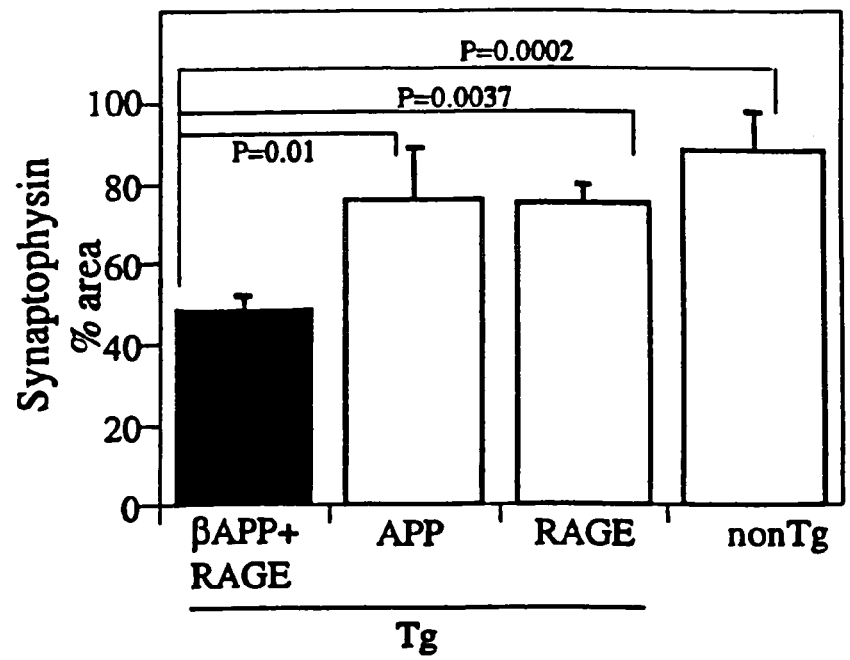
FIG. 12. Semiquantitative analysis of synaptophysin immunoreactivity in hippocampus of Tg PD-RAGE/hAPP, Tg PD-RAGE, Tg hAPP, and nontransgenic littermate control mice at 4 months of age.
Figure 13:
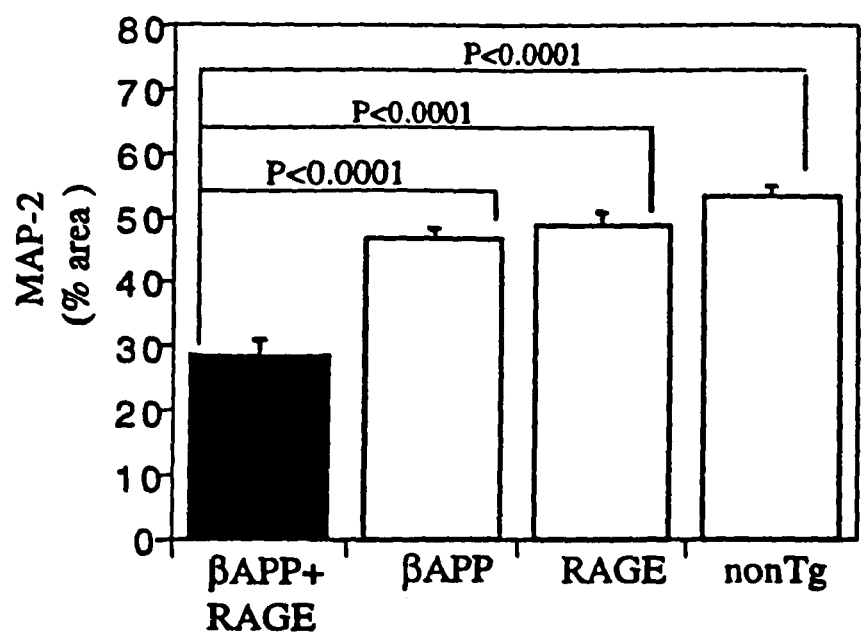
FIG. 13. Semiquantitative analysis of MAP-2 immunoreactivity in hippocampus of Tg PD-RAGE/hAPP, Tg PD-RAGE, Tg hAPP, and nontransgenic littermate control mice at 4 months of age.

These data were consistent with increased neuronal stress in Tg PD-RAGE/hAPP mice, but did not indicate whether the outcome of this stress would be neuroprotection or neurotoxicity. To analyze this situation neuropathologic studies were performed, and study of markers more clearly associated with toxicity, such as activated caspase 3, was undertaken. Immunostaining of hippocampus (lacunosum moleculare layer) from double transgenic mice (age 3-4 months) with antibody to synaptophysin demonstrated a reduction in the area of neuropil occupied by synaptophysin-labeled presynaptic terminals (FIG. 12). Similar studies with antibody to MAP-2 showed a reduction in the area of neuropil occupied by MAP-2-labeled dendrites (FIG. 13). Although stereologic studies will be required to determine actual neuronal loss, these results are consistent with evidence of neurotoxicity. Consistent with this impression, analysis of older double transgenic mice (8-9 months of age) showed increased staining with an antibody selective for the activated form of caspase 3 (FIGS. 14A1-4, 14B) and phosphorylated tau (AT8) (FIGS. 15A1-A4, 15B) in brains of double transgenic mice compared with the other groups.

Figure 16:
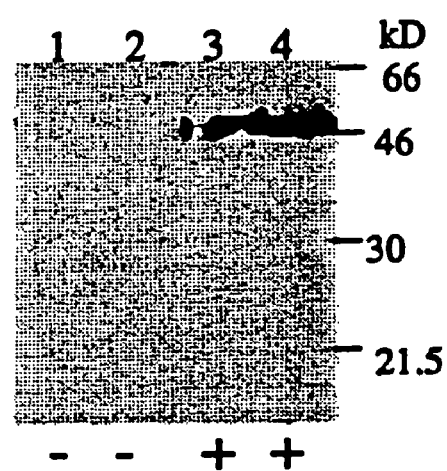
FIG. 16. Immunoblotting of E16 cortical neuron cultures with anti-human RAGE IgG. (+) indicates neurons obtained from Tg PD-RAGE mice and (-) indicates neurons are from nontransgenic littermate controls.
Figure 18:
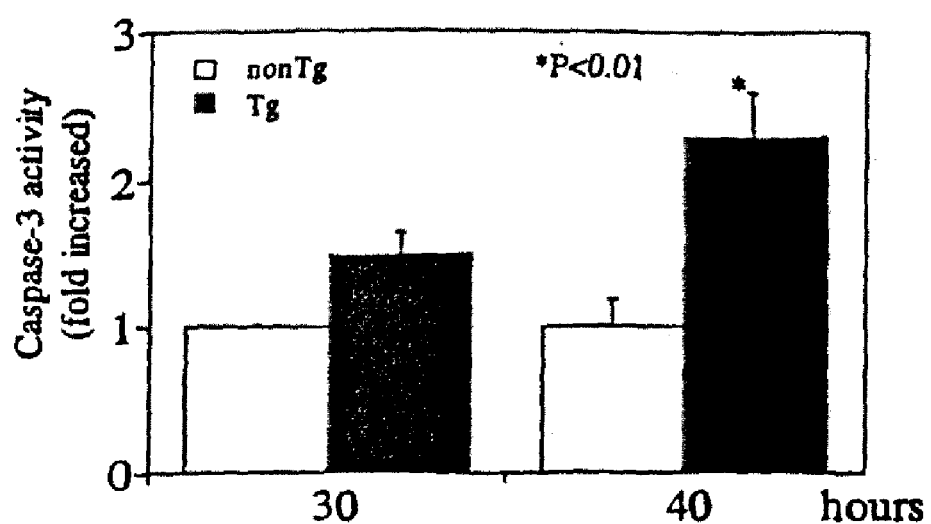
FIG. 18. Cortical neuron cultures (as in FIGS. 16-17) were exposed to preformed Aβ(1-40) fibrils (2 μM) for 30 or 40 hours, and caspase-3 activity was monitored. Neurons were derived from Tg PD- FIGS. 19A-19B. Volume of infarcted cerebral tissue was reduced in RAGE overexpressing transgenic mice compared with the control mice. The volume was reduced about 50% (p<0.05) in the transgenic mice compared with normal mice.

Culture of neurons from Tg PD-RAGE mice. Neuronal cultures were made from the cerebral cortex from E16 mouse embryos. These cultures were >90% neurons based on staining with anti-neurofilament antibody. Cultured neurons displayed high levels of RAGE expression based on immunoblotting (FIG. 16). Such neuronal cultures were incubated with preformed Aβ(1-40) fibrils (0.5 μM) for 2 hrs, and then nuclear extracts were prepared for EMSA using consensus probe for NF-kB. A gel shift band was observed in neuronal cultures from Tg PD-RAGE mice, but such a band was either not seen or present at much reduced intensity with samples from nontransgenic littermate control mice (FIG. 17A). That this was due to Aβ-RAGE interaction was confirmed by the dose-dependent inhibitory effect of anti-RAGE IgG, but not nonimmune IgG (FIG. 17B). To determine whether neurons overexpressing RAGE exposed to Aβ fibrils were being forced down a pathway of enhanced toxicity evidence of activated caspase 3 was sought. After 30-40 hrs of exposing Aβ fibrils to neurons from Tg PD-RAGE mice, increased caspase 3 activity was detected (FIG. 18). In contrast, under these conditions, neurons form nonTg littermates did not display increased caspase 3 activity.

Discussion

We have described the generation of Tg PD-RAGE mice which display increased expression of full-length RAGE in neurons. The use of these mice to analyze the contribution of RAGE to cellular responses in vitro and in vivo can be summarized according to three general categories:

1) analysis of neurons cultured from embryos of Tg PD-RAGE mice. Since neurons are nondividing cells and can only be transfected successfully with viral-based systems (which can alter cellular properties themselves), the cultured neurons from Tg PD-RAGE mice provide an unique system in which neurons overexpress human RAGE. These cells can be used to analyze the consequences of RAGE-ligand interaction for neuronal function, as shown by the activation of NF-kB and activation of caspase 3 in the above studies.

2) Tg PD-RAGE mice can be used to directly assess the effect of RAGE overexpression in settings such as, but not limited to, stroke (described above), viral/bacterial infections, other models of brain inflammation (such as experimental autoimmune encephalitis) etc.

3) Tg PD-RAGE mice can be crossbred with other transgenic animals, such as Tg hAPP to determine the consequences of RAGE overexpression in an environment in which the other transgene creates an unique environment in the brain. For example, the Tg hAPP mouse results in increased levels of Aβ. In this setting, the consequences of increased levels of Aβ in the context of neurons bearing elevated levels of RAGE can be studied. Another example would be crossbreeding of Tg PD-RAGE mice with mice deficient in the gene for apolipoprotein E[28], resulting in a model of accelerated atherosclerosis potentially with an exaggerated effect of RAGE.

In each case, the in vitro and in vivo systems based on Tg PD-RAGE mice or cells derived from them are ideal for studying RAGE inhibitors, as well as for dissecting contributions of RAGE to physiologic/pathophysiologic outcomes.

Example 2

Induction of Transient Middle Cerebral Artery in RAGE Transgenic Mice and Use of this Transgenic Mouse Model for Stroke in Humans Methods:

Induction of Transient Middle Cerebral Artery Occlusion in the Mouse

Induction of stroke in Tg PD-RAGE mice. Functional consequences of overexpression of RAGE were first assessed in response to ischemic stress, the transient middle cerebral artery occlusion model. Murine stroke model Mice (C57BL6/J, male) were subjected to stroke according to previously published procedures[32]. Following anesthesia, the carotid artery was accessed using the operative approach previously described in detail[33], including division/coagulation of the occipital and pterygopalatine arteries to obtain improved visualization and vascular access. A nylon suture was then introduced into the common carotid artery, and threaded up the internal carotid artery to occlude the origin of the right middle cerebral artery (MCA). Nylon (polyamide) suture material was obtained from United States Surgical Corporation (Norwalk, Conn.), and consisted of 5.0 nylon/13 mm length for 27-36 g mice, and 6.0 nylon/12 mm length for 22-26 g mice. After 45 minutes of occlusion, the suture was withdrawn to achieve a reperfused model of stroke. Although no vessels were tied off after the suture was removed, the external carotid arterial stump was cauterized to prevent frank hemorrhage.

Measurements of relative cerebral blood flow were obtained as previously reported[32-35] using a straight laser doppler flow probe placed 2 mm posterior to the bregma, and 6 mm to each side of midline using a stereotactic micromanipulator, keeping the angle of the probe perpendicular to the cortical surface. These cerebral blood flow measurements, expressed as the ratio of ipsilateral to contralateral blood flow, were obtained at baseline, and immediately prior to MCA occlusion, 45 minutes after MCA occlusion, and at several time points after withdrawal of the occluding suture.

Measurement of Cerebral Infarction Volumes: After 24 hours, animals were euthanized and their brains rapidly harvested. Infarct volumes were determined by staining serial cerebral sections with triphenyl tetrazolium chloride and performing computer-based planimetry of the negatively (infarcted) staining areas to calculate infarct volume (using NIH image software).

Neurological Exam: Prior to giving anesthesia, mice were examined for neurological deficit 23 h after reperfusion using a four-tiered grading system: a score of 1 was given if the animal demonstrated normal spontaneous movements; a score of 2 was given if the animal was noted to be turning towards the ipsilateral side; a score of 3 was given if the animal was observed to spin longitudinally (clockwise when viewed from the tail); and, a score of 4 was given if the animal was unresponsive to noxious stimuli. This scoring system has been previously described in mice[32-34], and is based upon similar scoring systems used in rats[36]. Immunostaining of cerebral cortex following induction of stroke in wild-type mice was performed as described above using a rabbit polyclonal antibody made using purified recombinant murine ABAD as the immunogen. Quantitation of microscopic images was accomplished with the Universal Imaging System.

Figure 19:
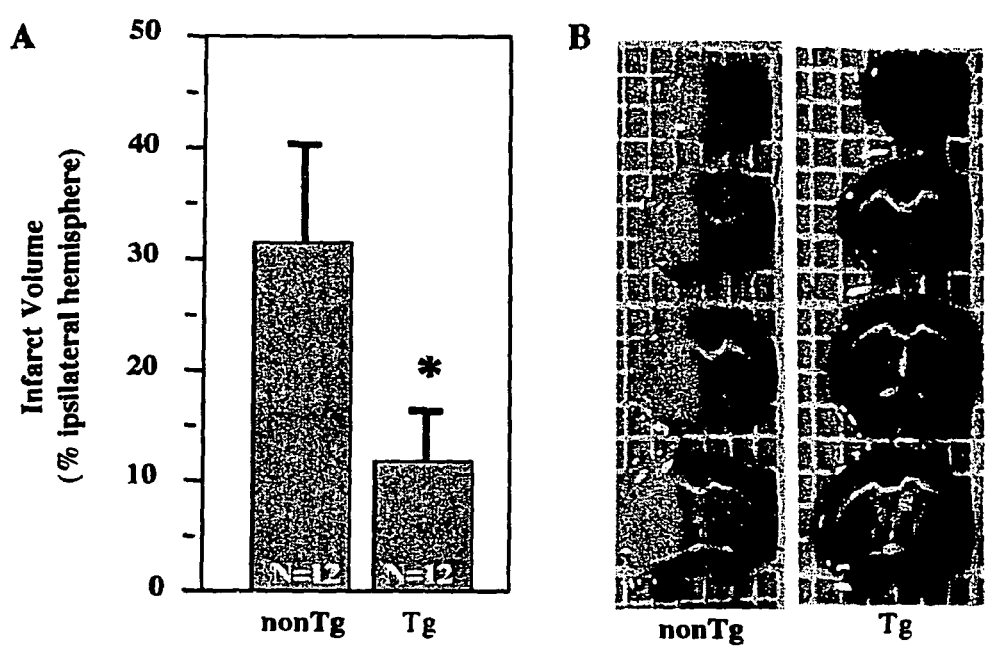
FIG. 19A shows results of studies in all mice.
FIG. 19B shows triphenyl tetrazolium chloride staining of selected cerebral sections.

Results:

Transgenic mice overexpressing RAGE under control of the platelet-derived growth factor promoter were subjected to transient middle cerebral artery occlusion along with non-transgenic littermates. Mice were 26-29 grams in weight and about 10 weeks old. The volume of infarcted cerebral tissue was reduced about 50% (P<0.05) in the transgenic mice compared with the controls (see FIG. 19A shows the results of studies in all mice, and FIG. 19B shows triphenyl tetrazolium chloride staining of selected cerebral sections). It is important to note that glucose levels were monitored in the animals before and after the ischemic episode, because of the known effect of hyperlgycemia on infarct volume. The animals remained normoglycemic throughout the procedure, These data indicate that overexpression of RAGE in neurons has a neuroprotective effect. Thus, it would be important to test potential RAGE inhibitors in such an animal to determine if they antagonized this protective property of the receptor. Figure legend: for the figure which you SHOULD send a messenger to pick up. Induction of stroke in transgenic mice overexpressing RAGE on the platelet-derived growth factor promoter: cerebral infarct volume (FIG. 19A) and results of triphenyl tetrazolium chloride staining of selected cerebral sections (FIG. 19B).

REFERENCES

1. Schmidt A-M, Yan S-D, Wautier J-L, Stern D M: Activation of RAGE: a mechanism for chronic dysfunction in diabetic vasculopathy and atherosclerosis. *Circ Res* 1999; 84:489-497
2. Hori O, Brett J, Nagashima M, Nitecki D, Morser J, Stern D M, Schmidt A M: RAGE is a cellular binding site for amphoterin: mediation of neurite outgrowth and co-expression of RAGE and amphoterin in the developing nervous system. *J Biol Chem* 1995; 270:25752-25761
3. Brett J, Schmidt A-M, Zou Y-S, Yan S-D, Weidman E, Pinsky D J, Neeper M, Przysiecki M, Shaw A, Migheli A, Stern D M: Tissue distribution of the receptor for advanced glycation endproducts (RAGE): expression in smooth muscle, cardiac myocytes, and neural tissue in addition to vasculature. *Am J Pathol* 1993; 143:1699-1712
4. Yan S-D, Chen X, Chen M, Zhu H, Roher A, Slattery T, Zhao L, Nagashima M, Morser J, Migheli A, Nawroth P, Stern D M, Schmidt A-M: RAGE and amyloid-beta peptide neurotoxicity in Alzheimer's disease. *Nature* 1996; 382:685-691
5. Park L, Raman K, Lee K, Lu Y, Ferran L, Chow W-S, Stern D, Schmidt A-M: Suppression of accelerated diabetic atherosclerosis by soluble receptor for AGE (sRAGE). *Nature Med* 1998; 4:1025-1031
6. Hofmann M, Drury S, Caifeng F, Qu W, Lu Y, Avila C, Kambhan N, Slattery T, McClary J, Nagashima M, Morser J, Stern D, Schmidt A-M: RAGE mediates a novel proinflammatory axis: the cell surface receptor for S100/calgranulin polypeptides. *Cell* 1999; 97:889-901
7. Yan S-D, Zhu H, Zhu A, Golabek A, Roher A, Yu J, Soto C, Schmidt A-M, Stern D M, Kindy M: Receptor-dependent cell stress and amyloid accumulation in systemic amyloidosis. *Nat Med* 2000; 6:643-651
8. Sasahara M, Fries J, Raines E, Gown A, Westrum L, Frosch M, Bonthron D, Ross R, Collins T: PDGF B-chain in neurons of the central nervous system, posterior pituitary and in a transgenic model. *Cell* 1991; 64:217-227
9. Kang D, Saitoh T, Chen X, Xia Y, Maslian E, Hansen L, Thomas R, Thal L, Katzman R: Genetic assocation of LRP with late-onset Alzheimer's disease. *Neurology* 1997; 49:56-61
10. Berezovska O, Frosch M, McLean P, Knowles R, Koo E, Kang D, Shen J, Lu F, Lux S, Tonegawa S, Hyman B: The Alzheimer-related gene presenilin 1 facilitates notch 1 in primary mammalian neurons. *Molec Brain Res* 1999; 69:273-280
11. Laemmli U: Cleavage of structural proteins during the assembly of the head of bacteriophage T4. *Nature* 1970; 227:680-685
12. Huang J, Kim L, Mealey R, March H, Zhang A, Tenner E, Connolly E, Pinsky D: Neuronal protection in stroke by an sLex-glycosylated complemetn inhibitory protein. *Science* 1999; 285:595-599
13. Connolly E S, Winfree C J, Stern D M, Solomon R A, Pinsky D J: Procedural and strain-related variables significantly affect outcome in a murine model of focal cerebral ischemia. *Neurosurg* 1996; 38:523-532
14. Connolly E S J, Winfree C J, Springer T A, Naka Y, Liao H, Yan S D, Stern D M, Solomon R A, Gutierrez-Ramos J-C, Pinsky D J: Cerebral protection in homozygous null ICAM-1 mice after middle cerebral artery occlusion. Role of neutrophil adhesion in the pathogenesis of stroke. *J Clin Invest* 1996; 97:209-216
15. Connolly E, Winfree C, Prestigiacomo C, Kim S, Choudhri T, Hoh B, Naka Y, Solomon R, Pinsky D: Exacerbation of cerebral injury in mice with express the P-selectin gene: identification of P-selectin blockade as a new target for treatment of stroke. *Circ Res* 1997; 81:304-310
16. Bederson J B, Pitts L H, Tsuji M: Rat middle cerebral artery occlusion: evaluation of the model and development of a neurologic examination. *Stroke* 1986; 17:472-476
17. Hsia A, Masliah E, McConlogue L, Yu G-Q, Tatsuno G, Hu K, Kholodenko D, Malenka R, Nicoll R, Mucke L: Plaque-independent disruption of neural circuits in Alzheimer's disease mouse models. *Proc Natl Acad Sci* (USA) 1999; 96:3228-3233
18. Terry R, Masliah E, Salmon D, Butters N, DeTeresa R, Hill R, Hansen L, Katzman R: Physical basis of cognitive alterations in Alzheimer disease: synapse loss is the major correlate of cognitive impairment. *Ann Neurol* 1991; 30:572-580
19. Zhan S, Beyreuther K, Schmitt H: Quantitative assessment of synaptophysin immunoreactivity of the corticla neuropil in various neurodegenerative diseases with dementia. Dementia 1993; 4:66-74
20. Dickson D, Crystal H, Bevona C, Honer W, Vincent I, Davies P: Correlation of synaptic and pathological markers incognition in the elderly. *Neurobiol Aging* 1995; 16:285-304
21. Sze C, Troncoso J, Kowas C, Mouton P, Price D, Martin J: Loss of presynaptic vesicle protein synaptophysin in hippocampus correlates with cognitive decline in Alzheimer disease. *J Neuropathol Exp Neurol* 1997; 56:933-944
22. Samuel W, Alford M, Hofstetter C, Hansen L: Dementia with Lewy bodies versus pure Alzheimer disease: differences in cognition, neuropathology, cholinergic dysfunction, and synapse density. *J Neuropathol Exp Neurol* 1997; 56:499-508
23. Brown D, Risser R, Bigio E, Tripp P, Stiegler A, Welch E, Eagan K, Hladik C, White C: Neocortical synatpic density and Braak stage in Lewy body variant of Alzheimer disease. *J Neuropathol Exp Neurol* 1998; 58:955-960
24. Masliah E, Achim C, Ge N, DeTeresa R, Terry R, Wiley C: The spectrum of human immunodeficiency virus-associated neocortical damage. *Ann Neurol* 1992; 32:321-329
25. Yan S-F, Tritto I, Pinsky D J, Liao H, May L, Stern D M: Induction of interleukin 6 (IL-6) by hypoxia in vascular cells: central role of the binding site for nuclear factor-IL-6. *J Biol Chem* 1995; 270:11463-11471
26. Dignam J, Lebovitz R, Roeder R: Accurate transcription initiation by RNA polymerase II in a soluble extract from isolated mammalian nuclei. *Nucl Acids Res* 1983; 11:1475-1489
27. White A, Zheng H, Galatis D, Maher F, Hesse L, Multhaup G, Beyreuther K, Masters C, Cappai R: Survival of cultured neurons from amyloid precursor protein knockout mice against Alzheimer's amyloid-β toxicity and oxidative stress. *J Neurosci* 1998; 18:6207-6217
28. Nakashima Y, Plump A, Raines E, Breslow J, Ross R: ApoE-deficient mice develop lesions of all phases of atherosclerosis throughout the arterial tree. *Arterioscler Thromb* 1994; 141:133-140

---

What is claimed is:

1. A transgenic mouse whose genome comprises a first DNA segment comprising:
   (a) a second DNA segment comprising a platelet derived growth factor B-chain promoter; and
   (b) a third DNA segment which encodes a human receptor for advanced glycation endproducts;
wherein the second DNA segment is operatively linked to the third DNA segment and the first DNA segment is integrated into the genome of the mouse; and wherein said mouse exhibits a reduced amount of infarcted cerebral tissue following induction of a transient middle cerebral artery occlusion in the mouse as compared to the amount exhibited by an otherwise identical mouse lacking said first DNA segment.

2. A method which comprises administering compound to the transgenic mouse of claim 1 and determining whether the mouse exhibits an increase in the amount of infarcted cerebral tissue following induction of a transient middle cerebral artery occlusion relative to the amount of infarcted cerebral tissue following such induction in an identical mouse in the absence of the compound.

* * * * *